US006352561B1

(12) United States Patent
Leopold et al.

(10) Patent No.: US 6,352,561 B1
(45) Date of Patent: Mar. 5, 2002

(54) IMPLANT DEPLOYMENT APPARATUS

(75) Inventors: Eric W. Leopold, Sunnyvale; Joseph C. Trautman, Santa Clara; Troy Thornton, San Francisco; Randy S. Chan, San Jose; Suresh S. Pai, Mountain View; Thomas G. Breton, Palo Alto, all of CA (US)

(73) Assignee: W. L. Gore & Associates, Newark, DE (US)

( * ) Notice: Subject to any disclaimer, the term of this patent is extended or adjusted under 35 U.S.C. 154(b) by 0 days.

(21) Appl. No.: 08/772,373

(22) Filed: Dec. 23, 1996

(51) Int. Cl.$^7$ .................................................. A61F 2/00
(52) U.S. Cl. ...................................... 623/123; 623/1.11
(58) Field of Search ............................. 623/1, 12, 1.11, 623/1.23

(56) References Cited

U.S. PATENT DOCUMENTS

| | | | |
|---|---|---|---|
| 2,638,093 A | 5/1953 | Kulick | |
| 3,029,819 A | 4/1962 | Starks | |
| 3,096,560 A | 7/1963 | Liebig | |
| 3,142,067 A | 7/1964 | Liebig | |
| 3,152,618 A | 10/1964 | Rothermal et al. | |
| 3,174,851 A | 3/1965 | Buehler et al. | |
| 3,351,463 A | 11/1967 | Rozner et al. | |
| 3,479,670 A | 11/1969 | Medell | |
| 3,514,791 A | 6/1970 | Sparks | |
| 3,562,820 A | 2/1971 | Braun | |
| 3,625,198 A | 12/1971 | Sparks | |
| 3,657,744 A | 4/1972 | Ersek | |
| 3,710,777 A | 1/1973 | Sparks | |
| 3,753,700 A | 8/1973 | Harrison | |
| 3,774,596 A | 11/1973 | Cook | |
| 3,805,301 A | 4/1974 | Liebig | |
| 3,866,247 A | 2/1975 | Sparks, deceased | |
| 3,866,609 A | 2/1975 | Sparks, deceased | |

(List continued on next page.)

FOREIGN PATENT DOCUMENTS

| | | |
|---|---|---|
| AU | B-42485/89 | 4/1990 |
| AU | B-34742/93 | 1/1993 |

(List continued on next page.)

OTHER PUBLICATIONS

International Search Report for PCT/US97/21641 mailed Apr. 15, 1999.

Notification of Transmittal of the International Preliminary Examination Report for PCT/US97/21641 mailed Apr. 21, 1999.

Blum, U. et al.; "Dacron Endografts for Infrarenal Abdominal Aortic Aneurysms: 2 Year Follow–Up"; Fifth international and Interdisciplinary Symposium on Endoluminal Stents and Grafts (Oct. 10–13, 1996) Washington, D.C., 2 pages total.

Blum, U. et al.; "Dacron Endografts for Infrarenal Abdominal Aortic Aneurysms: 2 Year Follow–Up"; Cardiovascular and Interventional Radiology. Springer, vol. 20, No. 1; Jan./Feb. 1997.

(List continued on next page.)

Primary Examiner—Michael J. Milano
(74) Attorney, Agent, or Firm—Morgan & Finnegan, LLP

(57) ABSTRACT

A delivery system including a restraining member maintains a collapsed implant in its collapsed state for delivery through a small passageway to a desired site in a mammalian body. Once the implant is positioned at the desired site, the restraining member is released so that the stent may expand or be expanded to its expanded state. In a preferred embodiment, the restraining member comprises a sheet of material that surrounds at least a portion of the collapsed stent. Portions of the restraining member are releasably coupled to one another with a low profile thread-like member or suture.

54 Claims, 25 Drawing Sheets

U.S. PATENT DOCUMENTS

| | | |
|---|---|---|
| 3,868,956 A | 3/1975 | Alfidi et al. |
| 3,927,422 A | 12/1975 | Sawyer |
| 3,938,524 A | 2/1976 | Sparks, deceased et al. |
| 3,949,073 A | 4/1976 | Daniels et al. |
| 3,953,566 A | 4/1976 | Gore |
| 3,974,526 A | 8/1976 | Dardik et al. |
| 3,993,045 A | 11/1976 | Ion |
| 4,011,861 A | 3/1977 | Enger |
| 4,047,252 A | 9/1977 | Liebig et al. |
| 4,130,904 A | 12/1978 | Whalen |
| 4,140,126 A | 2/1979 | Choudhury |
| 4,164,045 A | 8/1979 | Bokros et al. |
| 4,187,390 A | 2/1980 | Gore |
| 4,300,244 A | 11/1981 | Bokros |
| 4,306,318 A | 12/1981 | Mano et al. |
| 4,319,363 A | 3/1982 | Ketharanathan |
| 4,355,426 A | 10/1982 | MacGregor |
| 4,411,655 A | 10/1983 | Schreck |
| 4,424,208 A | 1/1984 | Wallace et al. |
| 4,425,908 A | 1/1984 | Simon |
| 4,488,911 A | 12/1984 | Luck et al. |
| 4,494,531 A | 1/1985 | Gianturco |
| 4,502,159 A | 3/1985 | Woodroof et al. |
| 4,503,569 A | 3/1985 | Dotter |
| 4,512,338 A | 4/1985 | Balko et al. |
| 4,517,687 A | 5/1985 | Liebig et al. |
| 4,530,113 A | 7/1985 | Matterson |
| 4,546,500 A | 10/1985 | Bell |
| 4,553,545 A | 11/1985 | Maass et al. |
| 4,557,764 A | 12/1985 | Chu |
| 4,562,596 A | 1/1986 | Kornberg |
| 4,580,568 A | 4/1986 | Gianturco |
| 4,582,640 A | 4/1986 | Smestad et al. |
| 4,592,754 A | 6/1986 | Gupte et al. |
| 4,604,762 A | 8/1986 | Robinson |
| 4,617,932 A | 10/1986 | Kornberg |
| 4,629,458 A | 12/1986 | Pinchuk |
| 4,641,653 A | 2/1987 | Rockey |
| 4,642,117 A | 2/1987 | Nguyen et al. |
| 4,647,416 A | 3/1987 | Seiler et al. |
| 4,649,922 A | 3/1987 | Wiktor |
| 4,655,771 A | 4/1987 | Wallsten |
| 4,665,906 A | 5/1987 | Jervis |
| 4,689,399 A | 8/1987 | Chu |
| 4,728,328 A | 3/1988 | Hughes et al. |
| 4,733,665 A | 3/1988 | Palmaz |
| 4,738,666 A | 4/1988 | Fuqua |
| 4,739,762 A | 4/1988 | Palmaz |
| 4,740,207 A | 4/1988 | Kreamer |
| 4,760,849 A | 8/1988 | Kropf |
| 4,816,028 A | 3/1989 | Kapadia et al. |
| 4,842,575 A | 6/1989 | Hoffman, Jr. et al. |
| 4,878,906 A * | 11/1989 | Lindemann .................... 623/1 |
| 4,892,539 A | 1/1990 | Koch |
| 4,957,504 A | 9/1990 | Chardack |
| 4,994,071 A | 2/1991 | MacGregor |
| 5,019,085 A | 5/1991 | Hillstead |
| 5,019,090 A | 5/1991 | Pinchuk |
| 5,035,706 A | 7/1991 | Giantureo et al. |
| 5,042,161 A | 8/1991 | Hodge |
| 5,064,435 A | 11/1991 | Porter |
| 5,066,298 A | 11/1991 | Hess |
| 5,067,957 A | 11/1991 | Jervis |
| 5,078,726 A | 1/1992 | Kreamer |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,424 A | 4/1992 | Hoffman, Jr. et al. |
| 5,122,154 A | 6/1992 | Rhodes |
| 5,123,917 A | 6/1992 | Lee |
| 5,127,919 A | 7/1992 | Ibrahim et al. |
| 5,133,732 A | 7/1992 | Wiktor |
| 5,139,480 A | 8/1992 | Hickle et al. |
| 5,147,370 A | 9/1992 | McNamara et al. |
| 5,151,105 A | 9/1992 | Kwan-Gett |
| 5,156,619 A | 10/1992 | Ehrenfeld |
| 5,161,547 A | 11/1992 | Tower |
| 5,162,430 A | 11/1992 | Rhee et al. |
| 5,163,958 A | 11/1992 | Pinchuk |
| 5,171,262 A | 12/1992 | MacGregor |
| 5,178,630 A | 1/1993 | Schmitt |
| 5,192,289 A | 3/1993 | Jessen |
| 5,192,307 A | 3/1993 | Wall |
| 5,195,984 A | 3/1993 | Schatz |
| 5,197,977 A | 3/1993 | Hoffman, Jr. et al. |
| 5,197,978 A | 3/1993 | Hess |
| 5,201,757 A | 4/1993 | Heyn et al. |
| 5,209,735 A | 5/1993 | Lazarus |
| 5,211,658 A | 5/1993 | Clouse |
| 5,213,580 A | 5/1993 | Slepian et al. |
| 5,217,483 A | 6/1993 | Tower |
| 5,221,261 A | 6/1993 | Termin et al. |
| 5,226,913 A | 7/1993 | Pinchuk |
| 5,232,446 A | 8/1993 | Arney |
| 5,236,447 A | 8/1993 | Kubo et al. |
| 5,242,451 A | 9/1993 | Harada et al. |
| 5,246,452 A | 9/1993 | Sinnott |
| 5,258,042 A | 11/1993 | Mehta |
| 5,264,276 A | 11/1993 | McGregor et al. |
| 5,271,410 A | 12/1993 | Wolzinger et al. |
| 5,276,276 A | 1/1994 | Gunn |
| 5,282,824 A | 2/1994 | Gianturco |
| 5,282,846 A | 2/1994 | Schmitt |
| 5,282,847 A | 2/1994 | Trescony et al. |
| 5,282,848 A | 2/1994 | Schmitt |
| 5,290,305 A | 3/1994 | Inoue |
| 5,306,261 A | 4/1994 | Alliger et al. |
| 5,306,294 A | 4/1994 | Wnston et al. |
| 5,314,472 A | 5/1994 | Fontaine |
| 5,324,304 A | 6/1994 | Rasmussen |
| 5,324,323 A | 6/1994 | Bui |
| 5,330,528 A | 7/1994 | Lazim |
| 5,336,254 A | 8/1994 | Brennen et al. |
| 5,342,348 A | 8/1994 | Kaplan |
| 5,342,387 A | 8/1994 | Summers |
| 5,344,426 A | 9/1994 | Lau et al. |
| 5,348,537 A | 9/1994 | Wiesner et al. |
| 5,354,308 A | 10/1994 | Simon et al. |
| 5,354,309 A | 10/1994 | Schnepp-Pesch et al. |
| 5,356,423 A | 10/1994 | Tihon et al. |
| 5,360,443 A | 11/1994 | Barone et al. |
| 5,366,472 A | 11/1994 | Hillstead |
| 5,366,473 A | 11/1994 | Winston et al. |
| 5,366,504 A | 11/1994 | Andersen et al. |
| 5,370,691 A | 12/1994 | Samson |
| 5,372,600 A | 12/1994 | Beyar et al. |
| 5,382,261 A | 1/1995 | Palmaz |
| 5,383,928 A | 1/1995 | Scott et al. |
| 5,385,580 A | 1/1995 | Schmitt |
| 5,387,235 A | 2/1995 | Chuter |
| 5,405,377 A | 4/1995 | Cragg |
| 5,405,378 A * | 4/1995 | Strecker ........................ 623/1 |
| 5,413,598 A | 5/1995 | Moreland |
| 5,421,955 A | 6/1995 | Lau et al. |
| 5,423,849 A | 6/1995 | Engelson et al. |
| 5,425,710 A | 6/1995 | Kahir et al. |
| 5,425,739 A | 6/1995 | Jessen |
| 5,443,500 A | 8/1995 | Sigwart |
| 5,449,373 A | 9/1995 | Pinchasik et al. |
| 5,453,084 A | 9/1995 | Moses |

| Patent | Date | Inventor |
|---|---|---|
| 5,456,713 A | 10/1995 | Chuter |
| 5,456,721 A | 10/1995 | LeGrand |
| 5,458,605 A | 10/1995 | Klemm |
| 5,458,615 A | 10/1995 | Klemm et al. |
| 5,464,449 A | 11/1995 | Ryan et al. |
| 5,476,506 A | 12/1995 | Lunn |
| 5,480,423 A | 1/1996 | Ravenscroft et al. |
| 5,484,444 A | 1/1996 | Braunschweiler et al. |
| 5,487,858 A | 1/1996 | Schmitt |
| 5,489,295 A | 2/1996 | Piplani et al. |
| 5,496,364 A | 3/1996 | Schmitt |
| 5,496,365 A | 3/1996 | Sgro |
| 5,499,994 A | 3/1996 | Tihon et al. |
| 5,507,767 A | 4/1996 | Maeda et al. |
| 5,507,769 A | 4/1996 | Marin et al. |
| 5,507,771 A | 4/1996 | Gianturco |
| 5,509,902 A | 4/1996 | Raulerson |
| 5,509,931 A | 4/1996 | Schmitt |
| 5,514,154 A | 5/1996 | Lau et al. |
| 5,522,822 A | 6/1996 | Phelps et al. |
| 5,522,880 A | 6/1996 | Barone et al. |
| 5,522,881 A | 6/1996 | Lentz |
| 5,522,961 A | 6/1996 | Leonhardt |
| 5,540,701 A | 7/1996 | Sharkey et al. |
| 5,540,712 A | 7/1996 | Kleshinkski et al. |
| 5,545,210 A | 8/1996 | Hess et al. |
| 5,545,211 A | 8/1996 | An et al. |
| 5,549,635 A | 8/1996 | Solar |
| 5,549,663 A | 8/1996 | Cottone, Jr. |
| 5,554,180 A | 9/1996 | Turk |
| 5,554,181 A | 9/1996 | Das |
| 5,554,182 A | 9/1996 | Dinh et al. |
| 5,556,413 A | 9/1996 | Lam |
| 5,562,724 A | 10/1996 | Vorwerk et al. |
| 5,562,726 A | 10/1996 | Chuter |
| 5,562,727 A | 10/1996 | Turk et al. |
| 5,571,166 A | 11/1996 | Dinh et al. |
| 5,571,169 A | 11/1996 | Plaia et al. |
| 5,571,172 A | 11/1996 | Chin |
| 5,571,173 A | 11/1996 | Parodi |
| 5,571,176 A | 11/1996 | Taheri |
| 5,575,815 A | 11/1996 | Slepian et al. |
| 5,575,816 A | 11/1996 | Rudnick et al. |
| 5,575,817 A | 11/1996 | Martin |
| 5,578,071 A | 11/1996 | Parodi |
| 5,591,197 A | 1/1997 | Orth et al. |
| 5,591,198 A | 1/1997 | Boyle et al. |
| 5,591,228 A | 1/1997 | Edoga |
| 5,591,229 A | 1/1997 | Parodi |
| 5,599,305 A | 2/1997 | Hermann et al. |
| 5,607,442 A | 3/1997 | Fischell et al. |
| 5,607,444 A | 3/1997 | Lam |
| 5,607,445 A | 3/1997 | Summers |
| 5,609,625 A | 3/1997 | Piplani et al. |
| 5,609,627 A | 3/1997 | Goicoechea et al. |
| 5,620,763 A | 4/1997 | House et al. |
| 5,622,188 A | 4/1997 | Plaia et al. |
| 5,626,561 A | 5/1997 | Butler et al. |
| 5,628,783 A | 5/1997 | Quiachon et al. |
| 5,628,784 A | 5/1997 | Strecker |
| 5,628,788 A | 5/1997 | Pinchuk |
| 5,632,763 A | 5/1997 | Glastra |
| 5,632,772 A | 5/1997 | Alcime et al. |
| 5,637,113 A | 6/1997 | Tartaglia et al. |
| 5,639,278 A | 6/1997 | Dereume et al. |
| 5,643,208 A | 7/1997 | Parodi |
| 5,647,380 A | 7/1997 | Campbell et al. |
| 5,649,978 A * | 7/1997 | Samson .................... 623/1 |
| 5,653,743 A | 8/1997 | Martin |
| 5,653,748 A | 8/1997 | Strecker |
| 5,662,614 A | 9/1997 | Edoga |
| 5,662,675 A | 9/1997 | Polanskyj Stockert et al. |
| 5,662,701 A | 9/1997 | Plaia et al. |
| 5,662,713 A | 9/1997 | Andersen et al. |
| 5,665,117 A | 9/1997 | Rhodes |
| 5,667,523 A | 9/1997 | Bynon et al. |
| 5,669,924 A | 9/1997 | Shaknovich |
| 5,669,930 A | 9/1997 | Igarashi |
| 5,674,276 A | 10/1997 | Andersen et al. |
| 5,676,671 A | 10/1997 | Inoue |
| 5,676,696 A | 10/1997 | Marcade |
| 5,676,697 A | 10/1997 | McDonald |
| 5,681,346 A | 10/1997 | Orth et al. |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,517 A | 12/1997 | Marin et al. |
| 5,697,970 A | 12/1997 | Schmitt et al. |
| 5,700,285 A | 12/1997 | Myers et al. |
| 5,700,286 A * | 12/1997 | Tartaglia .................... 623/1 |
| 5,709,657 A | 1/1998 | Zimmon |
| 5,713,917 A | 2/1998 | Leonhardt et al. |
| 5,716,365 A | 2/1998 | Goicoechea et al. |
| 5,718,724 A | 2/1998 | Goicoechea et al. |
| 5,718,973 A | 2/1998 | Lewis et al. |
| 5,720,776 A | 2/1998 | Chuter et al. |
| 5,723,003 A | 3/1998 | Winston et al. |
| 5,723,004 A | 3/1998 | Dereume et al. |
| 5,728,131 A | 3/1998 | Frantzen et al. |
| 5,728,150 A | 3/1998 | McDonald et al. |
| 5,730,698 A | 3/1998 | Fischell et al. |
| 5,732,572 A | 3/1998 | Litton |
| 5,735,892 A | 4/1998 | Myers et al. |
| 5,741,274 A | 4/1998 | Lenker et al. |
| 5,741,325 A | 4/1998 | Chaikof et al. |
| 5,749,825 A | 5/1998 | Fischell et al. |
| 5,749,880 A | 5/1998 | Banas et al. |
| 5,749,921 A * | 5/1998 | Lenker .................... 623/1 |
| 5,755,769 A * | 5/1998 | Richard .................... 623/1 |
| 5,769,882 A | 6/1998 | Fogarty et al. |
| 5,779,732 A * | 7/1998 | Amundson .................... 623/1 |
| 5,782,904 A | 7/1998 | White et al. |
| 5,800,521 A | 9/1998 | Orth |
| 5,800,522 A | 9/1998 | Campbell et al. |
| 5,800,524 A | 9/1998 | Borghi |
| 5,810,870 A | 9/1998 | Myers et al. |
| 5,824,041 A | 10/1998 | Lenker et al. |
| 5,843,069 A | 12/1998 | Butler et al. |
| 5,843,171 A | 12/1998 | Campbell et al. |
| 5,865,723 A | 2/1999 | Love |
| 5,868,704 A | 2/1999 | Campbell et al. |
| 5,873,906 A | 2/1999 | Lau et al. |
| 5,876,432 A | 3/1999 | Lau et al. |
| 5,888,243 A | 3/1999 | Silvestrini |
| 5,919,225 A | 7/1999 | Lau et al. |
| 5,925,061 A | 7/1999 | Ogi et al. |
| 5,925,075 A | 7/1999 | Myers et al. |
| 5,961,546 A | 10/1999 | Robinson et al. |
| 5,972,441 A | 10/1999 | Campbell et al. |
| 5,976,650 A | 11/1999 | Campbell et al. |
| 5,993,489 A | 11/1999 | Lewis et al. |
| 6,001,123 A | 12/1999 | Lau |
| 6,015,429 A | 1/2000 | Lau et al. |
| 6,015,431 A | 1/2000 | Thornton et al. |
| 6,017,362 A | 1/2000 | Lau |
| 6,019,787 A | 1/2000 | Richard et al. |
| 6,019,788 A | 1/2000 | Butters et al. |

| | | | |
|---|---|---|---|
| 6,025,044 A | 2/2000 | Campbell et al. |
| 6,027,779 A | 2/2000 | Campbell et al. |
| 6,027,811 A | 2/2000 | Campbell et al. |
| 6,042,605 A | 3/2000 | Martin et al. |
| 6,048,484 A | 4/2000 | House |
| 6,086,604 A | 7/2000 | Fischell et al. |
| 6,120,477 A | 9/2000 | Campbell et al. |
| 6,139,572 A | 10/2000 | Campbell et al. |
| 6,159,565 A | 12/2000 | Campbell et al. |
| 6,165,210 A | 12/2000 | Lau et al. |
| 6,193,745 B1 | 2/2001 | Fogarty et al. |
| 6,203,568 B1 | 3/2001 | Lombardi et al. |

FOREIGN PATENT DOCUMENTS

| | | |
|---|---|---|
| CA | 2026604 | 4/1991 |
| CA | 2079417 | 4/1993 |
| DE | 37 24 514 A1 | 2/1989 |
| DE | 39 18736 A1 | 12/1990 |
| DE | 41 37 857 A1 | 5/1992 |
| DE | 196 17 823 A1 | 11/1997 |
| EP | 0 382 014 A1 | 8/1990 |
| EP | 0 408 245 A1 | 1/1991 |
| EP | 0 418 677 A1 | 3/1991 |
| EP | 0 423 916 B1 | 4/1991 |
| EP | 0 435 518 A1 | 7/1991 |
| EP | 0 464 755 A1 | 1/1992 |
| EP | 0 472 731 A1 | 4/1992 |
| EP | 0 540 290 B1 | 5/1993 |
| EP | 0 551 179 A1 | 7/1993 |
| EP | 0 556 850 A1 | 8/1993 |
| EP | 0 565 251 A1 | 10/1993 |
| EP | 0 667 131 A2 | 1/1995 |
| EP | 0 689 806 A2 | 5/1995 |
| EP | 0 686 379 B1 | 12/1995 |
| EP | 0 696 447 A2 | 2/1996 |
| EP | 0 701 800 A1 | 3/1996 |
| EP | 0 705 577 A1 | 4/1996 |
| EP | 0 716 834 A1 | 6/1996 |
| EP | 0 747 020 A2 | 12/1996 |
| FR | 2 678 508 | 8/1993 |
| GB | 1 506 432 | 4/1978 |
| GB | 1 567 122 | 5/1980 |
| GB | 1 355 373 | 6/1994 |
| JP | 2-174859 | 7/1990 |
| JP | 6-007454 | 1/1994 |
| JP | 6-181993 | 7/1994 |
| JP | 7-500272 T | 1/1995 |
| JP | 7-024688 | 3/1995 |
| JP | 8-509899 T | 10/1996 |
| SU | 1635980 A1 | 12/1988 |
| WO | WO 88/06026 | 8/1988 |
| WO | WO 90/04982 | 5/1990 |
| WO | WO 92/03107 | 3/1992 |
| WO | WO 92/04097 | 3/1992 |
| WO | WO 92/06734 | 4/1992 |
| WO | WO 92/09246 | 6/1992 |
| WO | WO 93/13825 | 7/1993 |
| WO | WO 93/17636 | 9/1993 |
| WO | WO 93/19803 | 10/1993 |
| WO | WO 93/19804 | 10/1993 |
| WO | WO 93/22984 | 11/1993 |
| WO | WO 93/22986 | 11/1993 |
| WO | WO 93/22989 | 11/1993 |
| WO | WO 94/00179 | 1/1994 |
| WO | WO 94/01483 | 1/1994 |
| WO | WO 94/04097 | 3/1994 |
| WO | WO 94/12136 | 6/1994 |
| WO | WO 94/15549 | 7/1994 |
| WO | WO 95/01466 | 2/1995 |
| WO | WO 95/05131 | 2/1995 |
| WO | WO 95/05132 | 2/1995 |
| WO | WO 95/09586 | 4/1995 |
| WO | WO 95/21592 | 8/1995 |
| WO | WO 95/26695 | 10/1995 |
| WO | WO 96/10967 | 4/1996 |
| WO | WO 96/18360 | 6/1996 |
| WO | WO 96/18361 | 6/1996 |
| WO | WO 96 24306 | 8/1996 |
| WO | WO 97/21402 | 6/1997 |
| WO | WO 97/21403 | 6/1997 |
| WO | WO 97/21641 | 6/1997 |
| WO | WO 98/30173 | 7/1998 |

OTHER PUBLICATIONS

Chuter et al.; "Bifurcated stent–grafts for AAA: 3 year follow–up"; Abstracts from the Seventh International Course on Peripheral Vascular Intervention; J. Endovas. Surg. (1996) 3:453.

Chuter et al.; "Bifurcated stent–grafts for AAA: 3 year follow–up"; *Fifth International and Interdisciplinary Symposium on Endoluminal Stents and Grafts* (Oct. 10–13, 1996) Washington, D.C., 2 pages total.

Cragg et al., "Nitinol Intravascular Stent; Results of Pre–clinical Evaluation", Radiology 189(3): 775–778 (1993).

Cragg, "Percutaneous Femoropopliteal Graft Placement" Radiology 187(3): 643–648 (1993).

Cragg, et al.; "Percutaneous Femoropopliteal Graft Placement" Journal of Vascular and Interventional Radiology 4(4): 455–462 (1993).

Dereume, JP et al.; "Endoluminal Treatment Of Abdominal Aortic Aneurysm with the Corvita Endovascular Graft, Results of a Single–Center, Prospective Feasibility Study of 90 Patients"; *Abstracts from the Seventh International Course on Peripheral Vascular Intervention* J. Endovasc. Surg. (1996) 3:460–461.

Hagen et al., "Self–Expandable Macroporous Nitinol Stents for Transfemoral Exclusion of Aortic Aneurysm in Dogs" Cardiovascular Intervention Radiology 16:339–342 (1993).

Katzen et al., "initial experience performing combined surgical/interventional procedures in the interventional suite" *Abstracts from the Seventh International Course on Peripheral Vascular Intervention J. Endovasc. Surg.* (1996) 3:467.

Laborde et al, "Intraluminal Bypass of Abdominal Aortic Aneurysm Feasibility Study" Radiology 184:185–190 (1992).

Moore et al., "Transfemoral endovascular repair of abdominal aortic aneurysm: Result of the North American EVT phase 1 trial" J. Vasc. Surg. (1996) 23:543–552.

Parodi et al., "long–term follow–up of AAA endoluminal repair" Abstracts from the Seventh International Course on Peripheral Vascular Intervention. J. Endovasc. Surg. (1996) 3:335.

Product Brochure for Catheters, Guidewires, and Stents (no date) *Schneider* (USA) Inc., Pfizer Hospital Products Group, 5905 Nathan Lane, Minneapolis, Minnesota, 55442.

Product Brochure for *Cook–ZTM Stents*, Gianturco–Rosch Biliary Design, CookR, A Cook Groups Company, P.O. Box 489, Bloomington, IN, 47402, U.S.A., 4 pages total, (1989).

Product Brochure for *PalmazTM* Balloon–Expandable Stent, Johnson & Johnson Interventional Systems, 40 Technology Drive, P.O. Box 4917, Warren, NJ, 07059, 2 pages total, (1990).

Product Brochure for the Cragg stent and Cragg EndoPro System 1 *MinTecTm* Minimally Invasive Technologies, 4 pages total.

White et al., "Endoleak following endoluminal repair of AAA: Diagnosis, significance, and amanagement" *Abstracts from the Seventh International Course on Peripheral Vascular Intervention J. Endovasc. Surg.* (1996) 3:339–340.

Wilson et al.; "A self expanding bifurcated endovascular graft for Abdominal Aortic Aneurysm Repair. An Initial Study in a Canine Model" ASAIO Journal 42(5): 386–393 (1996).

World Medical News, World Medical manufacturing Corporation, 13794 NW 4th Street, Bldgs. 210 & 211, Sunrise, Florida, 33325 U.S.A., vol. 5, Issue 3 (Jul. 1996) 3 pages total.

U.S. application No. 08/871,427, Lau, et al., filed Jun. 9, 1997, pending.

U.S. application No. 08/896,373, Lau et al., filed Aug. 18, 1997, pending.

U.S. application No. 09/207,944, Vonesh et al., filed Dec. 9, 1998, response.

U.S. application No. 09/235,214, Brauker et al., filed Jan. 22, 1999.

U.S. application No. 09/235,458, Vonesh et al., filed Jan. 22, 1999, response.

U.S. application No. 09/306,522, Myers, filed May 06, 1999.

U.S. application No. 09/376,931, Martin, et al., filed Aug. 13, 1999, pending.

U.S. application No. 09/408,866, Brenton et al., filed Sep. 30, 1999, response.

U.S. application No. 09/488,229, Cully et al., filed Jan. 20, 2000.

U.S. application No. 09/489,604, Vonesh et al., filed Jan. 20, 2000.

U.S. application No. 09/510,937, Goffena et al., filed Feb. 22, 2000, response.

* cited by examiner

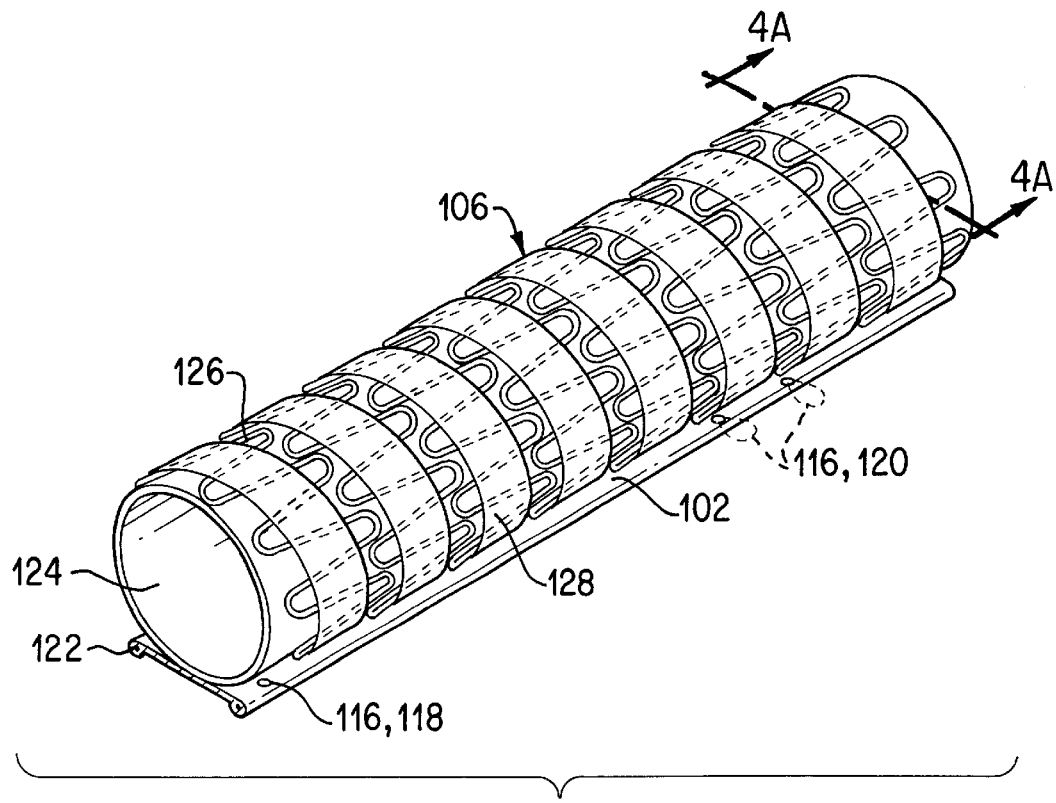
FIG. 3
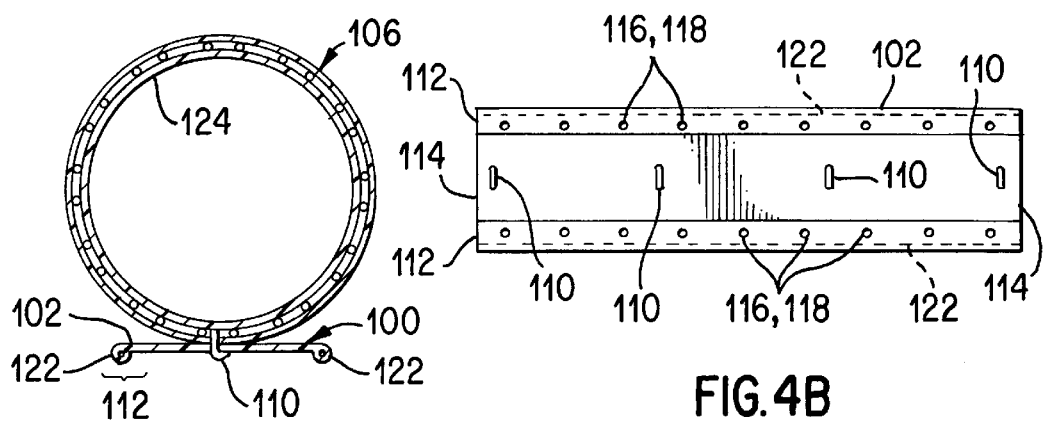
FIG. 4A
FIG. 4B

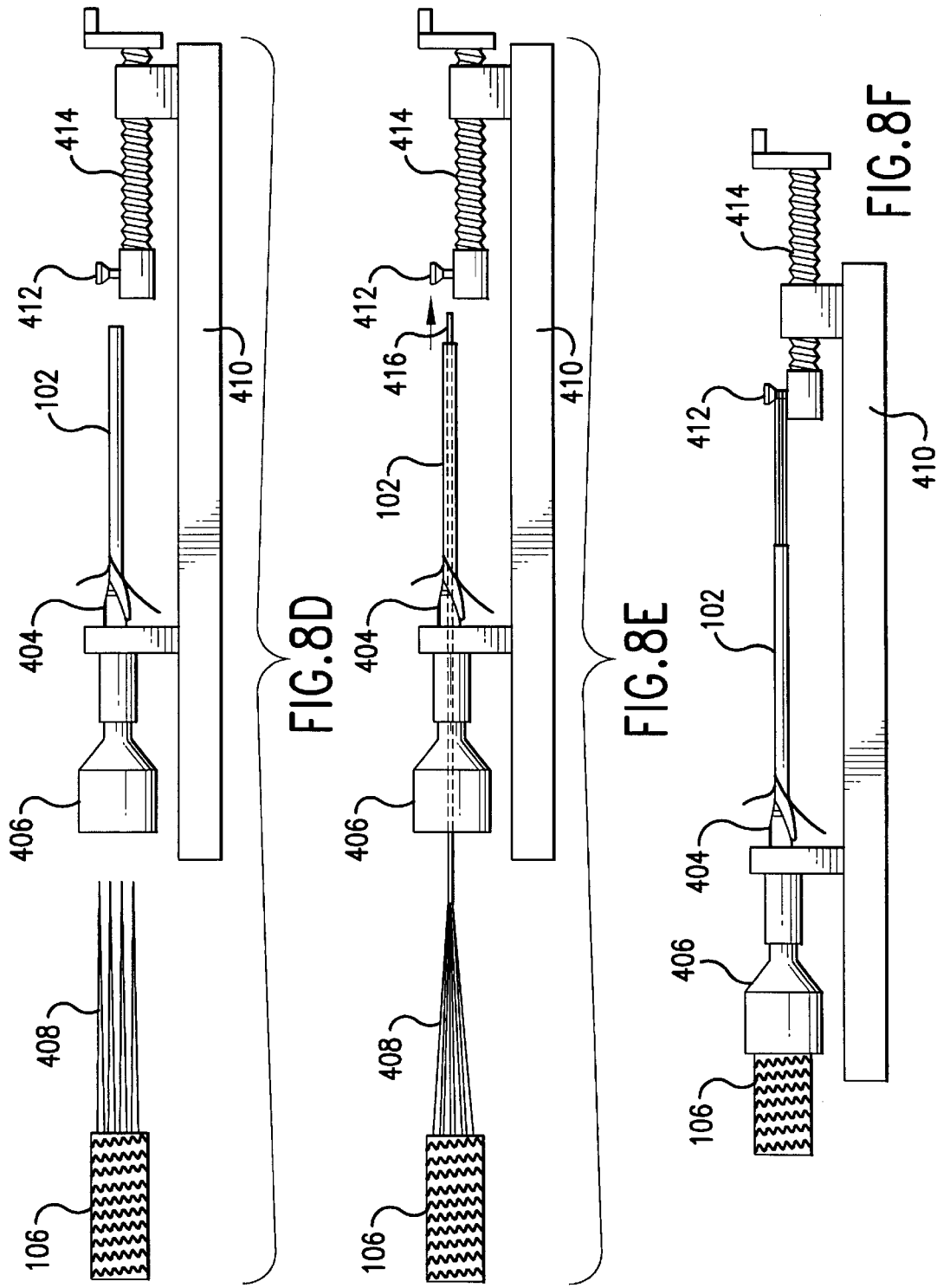

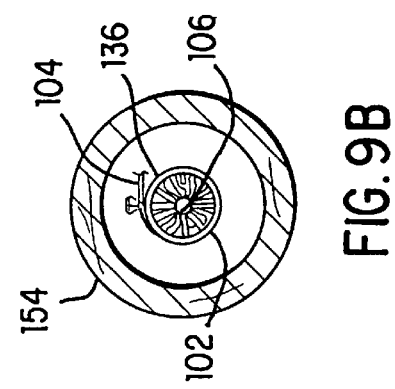
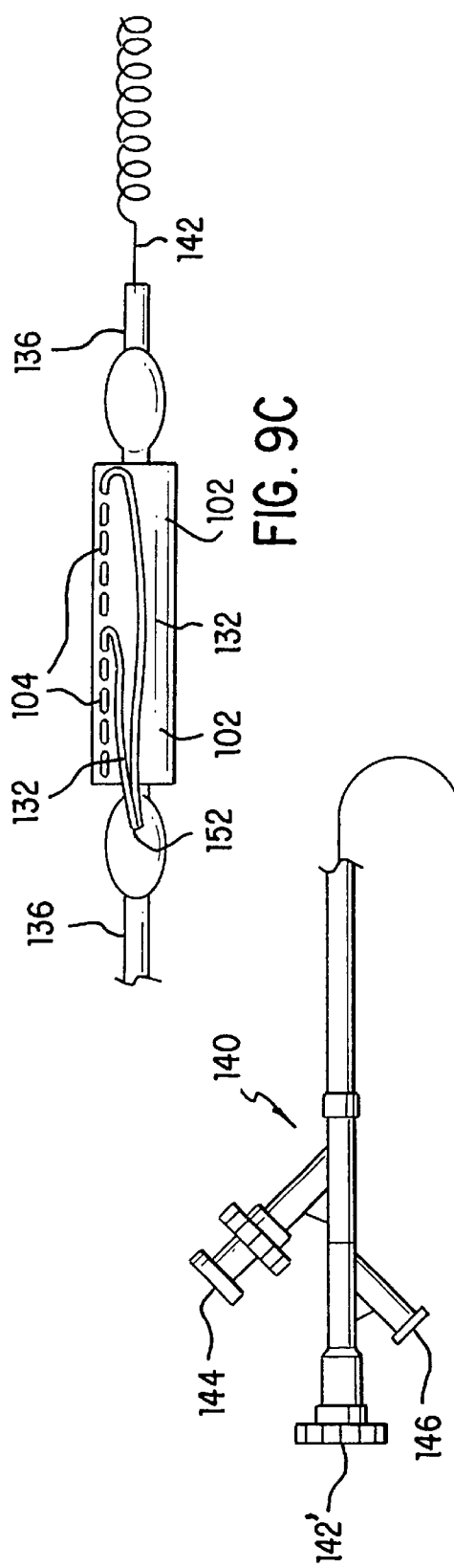
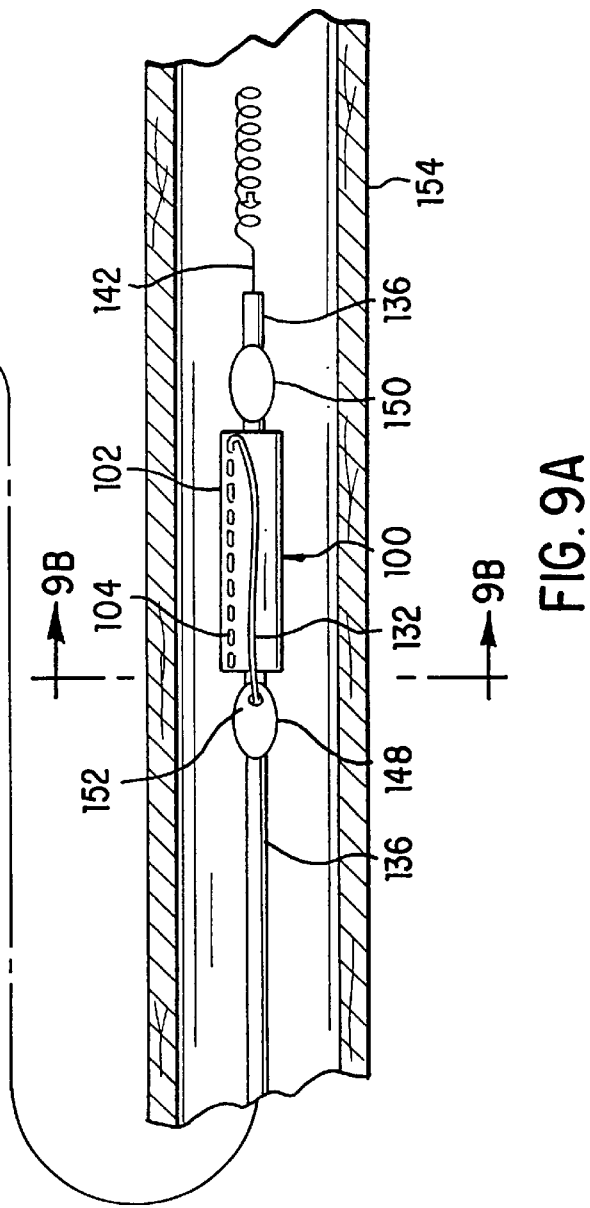

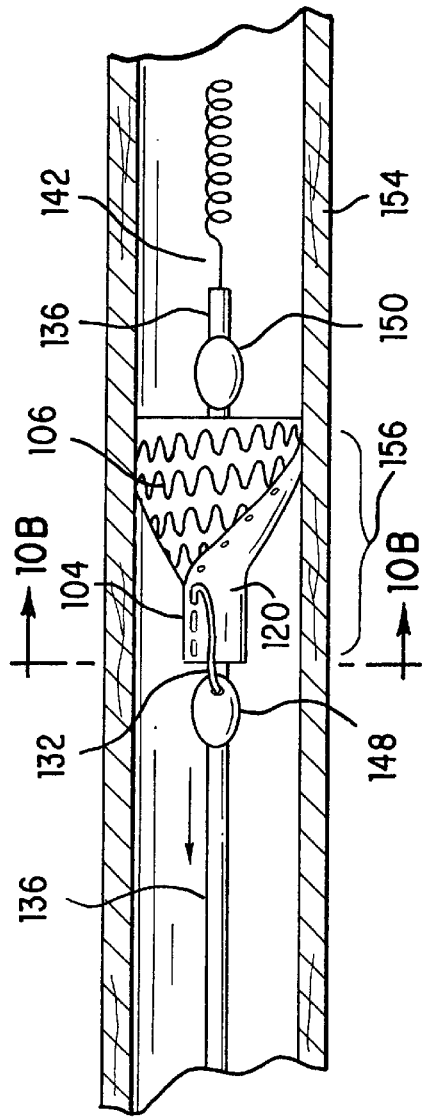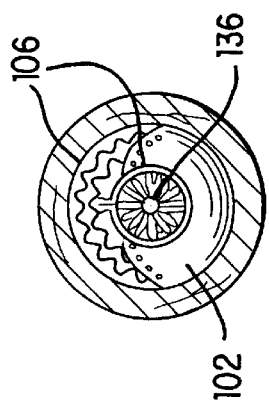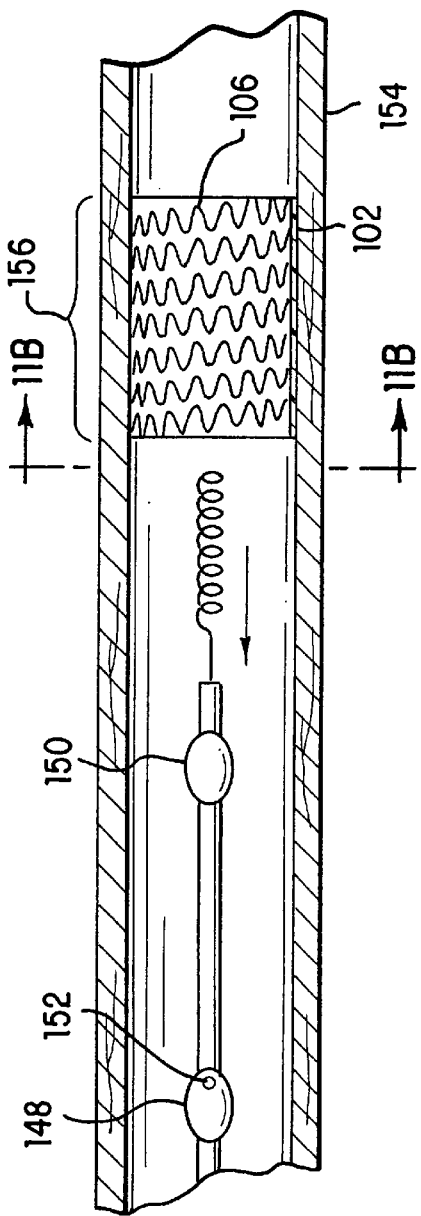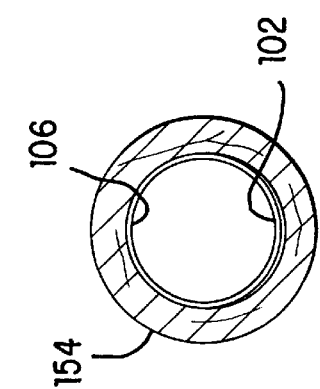

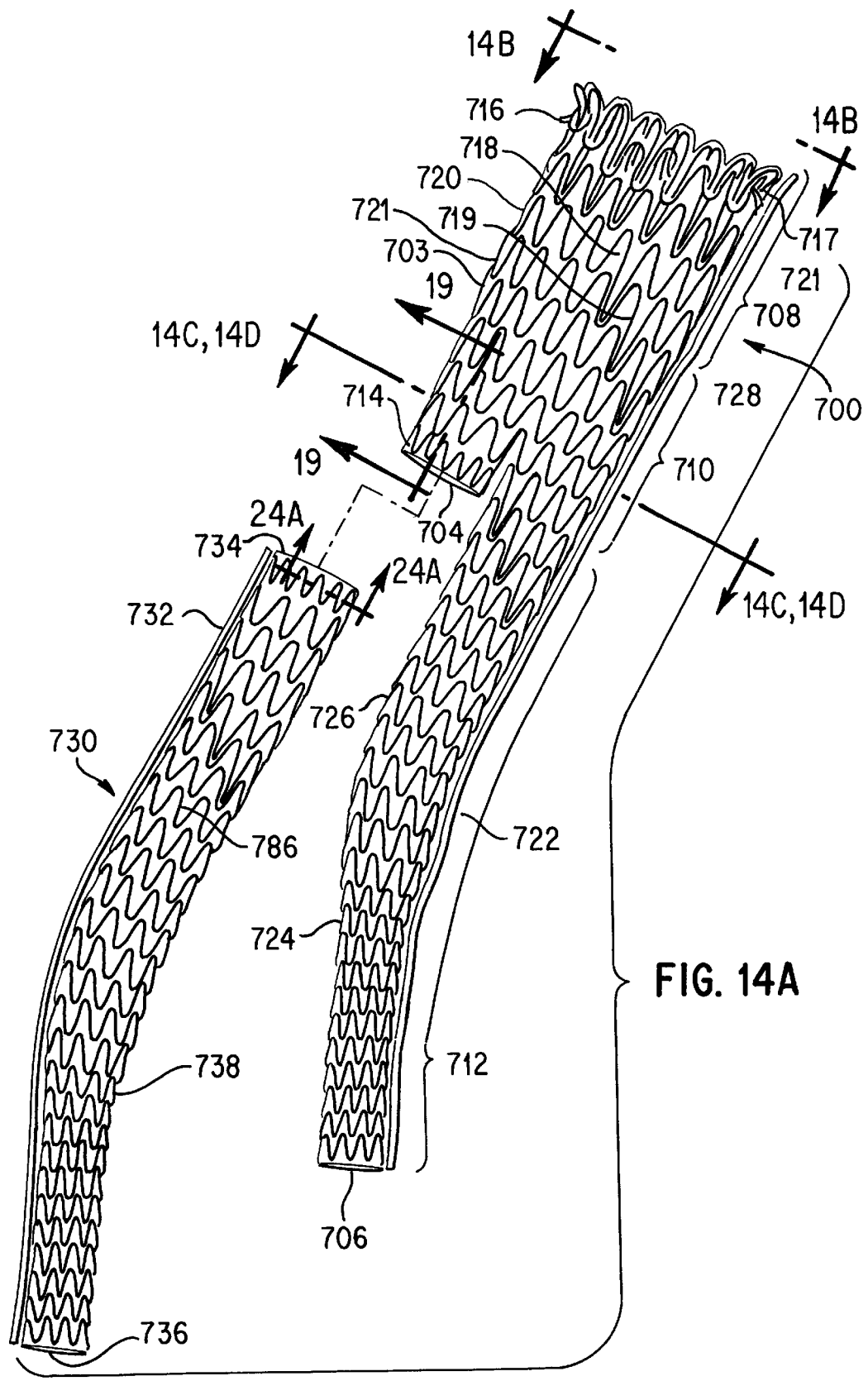

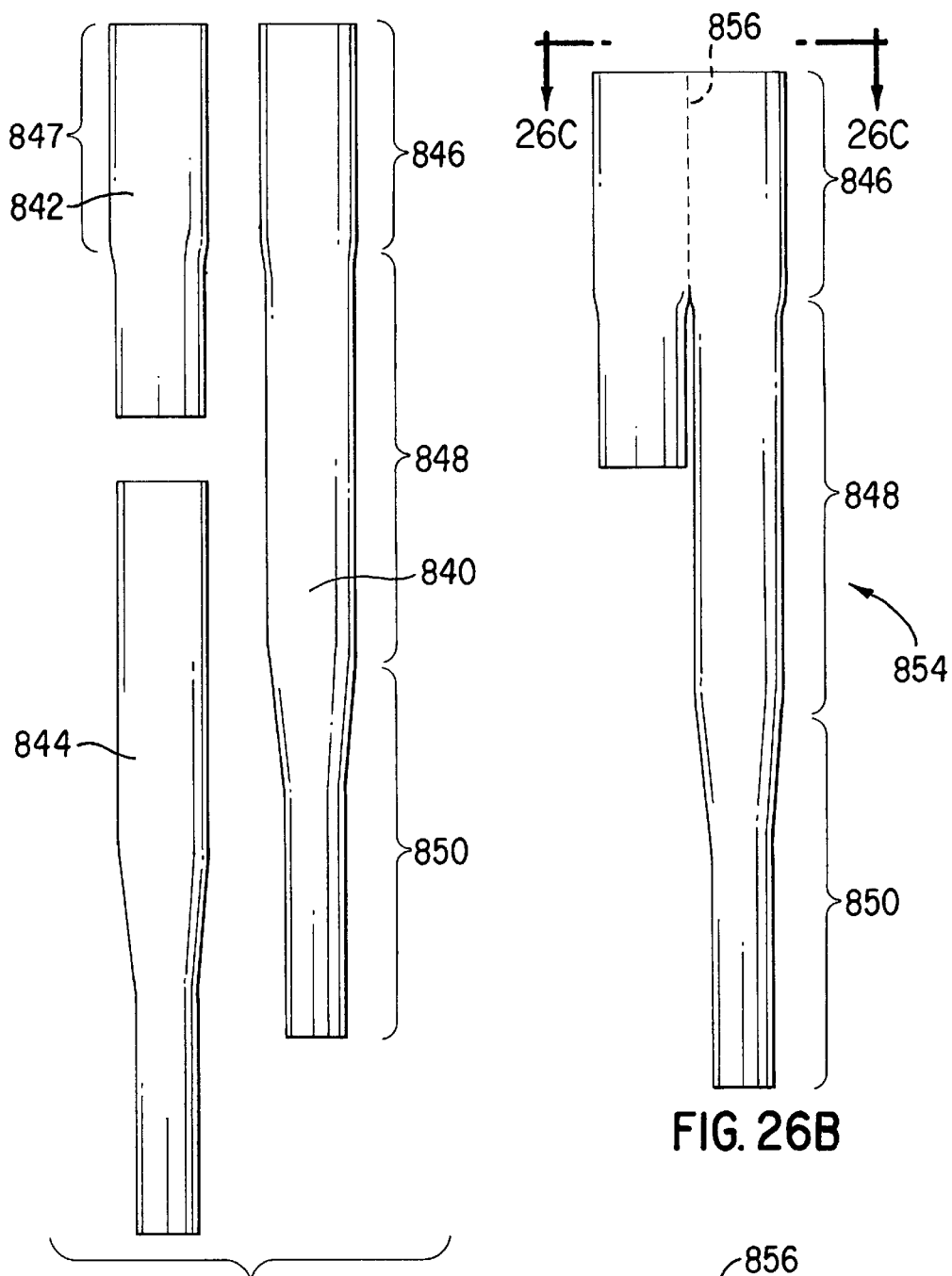
FIG. 26A
FIG. 26B
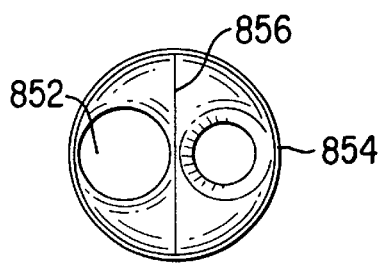
FIG. 26C

IMPLANT DEPLOYMENT APPARATUS

TECHNICAL FIELD

This invention relates generally to implants for repairing ducts and passageways in the body. More specifically, the invention relates to implant deployment apparatus.

BACKGROUND ART

Treatment or isolation of vascular aneurysms or of vessel walls which have been thickened or thinned by disease has traditionally been performed via surgical bypassing with vascular grafts. Shortcomings of this procedure include the morbidity and mortality associated with surgery, long recovery times after surgery, and the high incidence of repeat intervention needed due to limitations of the graft or of the procedure.

Vessels thickened by disease may be treated less invasively with stents which mechanically hold vessels open. In some instances, stents may be used subsequent to or as an adjunct to a balloon angioplasty procedure. Stents also have been described in conjunction with grafts where the graft is intended to provide a generally smooth interface with blood flowing through the vessel.

Generally, it is important that the stent or stent-graft be accurately deployed so that it may be positioned at the desired location. Endovascular stent or stent-graft deployment can be summarized as a two-step process. The first step is moving the stent within the vasculature to a desired location. The stent or stent-graft may be self-expanding or balloon expandable. In both cases, the implant is typically delivered in a collapsed state to facilitate delivery through relatively small vessel lumens. The second step involves some method of "locking" the stent or stent-graft into its final geometry so that it will remain implanted in the desired location.

A number of techniques for delivering self-expanding or balloon expandable stents and stent-grafts are known. In the case of a self-expanding stent or stent-graft, a restraining mechanism typically is used to keep the stent or stent-graft in its collapsed state during delivery. The restraining mechanism is later removed to allow the stent or stent-graft to expand and engage the vessel wall at the desired implantation site. In the case of a balloon expandable stent or stent-graft, a restraining mechanism typically keeps the expandable device in a collapsed position during delivery with an inflatable balloon positioned within the collapsed device. The restraining mechanism is later removed to allow for inflation of the balloon which causes the stent or stent-graft to expand so that it engages the vessel wall. Generally, tubular sheaths or tying elements, which may be in the form of a filament or thread, have been described to restrain the collapsed devices.

U.S. Pat. No. 4,878,906, to Lindemann et al., discloses balloon expandable stent-grafts which are deployed through a tubular sheath. The stent-grafts are forwarded in a collapsed state along the vessel until they are in the correct location where the sheath is withdrawn, allowing expansion of the balloon within the stent-graft. After the balloon has expanded the stent-graft into final position, the balloon is deflated and drawn back into the tubular sheath. An alternative deployment method disclosed by Lindemann et al., dispenses with the tubular sheath and uses a "thread" wrapped around the stent-graft and balloon which can be withdrawn when balloon inflation is desired.

Pinchuk, U.S. Pat. No. 5,019,090, shows a helically wrapped spring stent which is deployed with a balloon expansion catheter through a "sheath" which holds the stent and balloon catheter in a generally compressed state. Once the stent and balloon have been forwarded into the correct position along a lumen, the sheath is withdrawn. The balloon is then inflated, deflated, and withdrawn, leaving the stent in final implantation position.

U.S. Pat. No. 5,246,452, to Sinnott, discloses a porous vascular graft which is implanted with a tear-away removable nonporous sheath. Once the graft has been forwarded into the desired position, circulation is restored to the area and blood is allowed to clot inside of the porous graft. After five minutes of clotting, the nonporous sheath can be removed by cutting or by pulling a string which tears the sheath and pulls it away.

U.S. Pat. No. 5,344,426, to Lau et al., discloses an expandable stent which is preferably self locking when expanded. The stent is positioned over an expandable member such as a balloon catheter and covered by a one or two layer sheath which is connected to a guidewire. When the assembly of sheath, stent, and expandable member has been forwarded to the desired position, the sheath is removed by moving the guidewire distally. With the sheath pulled off of the stent, the expandable member can be activated to expand the stent into its final position.

U.S. Pat. No. 5,366,473, to Winston et al., discloses an assembly in which a vascular graft is held in a compressed state over a pair of stents by a sheath. The stents take the form of flexible sheets wound around a spool. After the spool has been inserted to the correct endovascular site, the sheath is withdrawn allowing the stents to unwind and press the graft against the vessel walls.

Strecker, U.S. Pat. No. 5,405,378, discloses an expandable prosthesis which is held in radially compressed condition by a releasable sheath. The sheath can be a strippable meshwork which allows the compressed prosthesis to expand when the meshwork is controllably unraveled.

Generally, the mechanisms described above involve a number of components that may increase operational complexity. In addition, the size and mechanical properties of these mechanisms may limit deliverability of implants in small vessels. Delivery accuracy also may be a problem as discussed.

The diameter of conventional telescoping stent sheaths may contribute to undesirable friction with the delivery catheter as the sheath is pulled from the stent and over a push rod during deployment. This may make deployment accuracy difficult to control. Push rods, which are used to push the stent through the delivery catheter and which typically have a length of up to about 100 cm, also may contribute to undesirable friction with the catheter. This problem may be exacerbated where the catheter bends along its path in the vasculature. The sheath may also reposition the stent as it is retracted.

DISCLOSURE OF THE INVENTION

The present invention generally involves a delivery apparatus for an implant, such as a stent or stent-graft. The delivery system generally comprises a sheet of material adapted to extend around at least a portion of a collapsed implant, such as a collapsed stent or stent-graft. The sheet of material may form a tubular member when extending around at least a portion of a collapsed member. The system also may include a coupling member for coupling portions of the sheet together to maintain the implant in its collapsed state during delivery to a desired site in a mammalian body. With this construction a smooth interface between the collapsed stent and a vessel lumen, as compared to thread-like restraining members, may be achieved.

According to another aspect of the invention, the sheet may be constructed of a thin material which does not significantly contribute to the structural rigidity or cross-sectional profile to the delivery assembly. This construction may also eliminate the need for external sheathing or a guide catheter and is believed to advantageously increase the ability of the surgeon to deliver the device to relatively remote sites and through small tortuous vasculature. In addition, the sheet may comprise implantable material so that after release it may remain with the stent at the desired site.

According to another embodiment of the invention, an assembly comprising a stent and a restraining member coupled to the stent is provided. The stent has a collapsed and an expanded state and the restraining member comprises a sheet of material adapted to be wrapped around at least a portion of the stent when the stent is in the collapsed state. Portions of the sheet are adapted for coupling to one another to maintain the sheet wrapped around at least a portion of the stent in its collapsed state. Thus, in one configuration, portions of the sheet are releasably coupled to one another so that the sheet maintains the stent in its collapsed state.

According to another aspect of the invention, the portions of the sheet that may be coupled to one another may be coupled with a filament or thread-like member. The stent may be expanded (or allowed to expand when a self-expanding stent is used) after the thread-like coupling member is removed such as by being remotely pulled by a pull line, which may be an extension of the coupling member. Since the pull line may also have a thread-like low profile, friction with the catheter, through which the pull line is pulled, and the pull line is minimized. It is believed that such construction may further facilitate deployment accuracy.

According to another aspect of the invention, multiple restraining members may be used. Alternatively, multiple coupling members may be used to couple multiple portions of one or more restraining members. These constructions can reduce deployment time and may reduce the time in which fluid flow may disturb the position of the implant as it is deployed.

According to another aspect of the invention, an assembly comprises a stent and a restraining member coupled to the stent. The stent has a collapsed and an expanded state and first and second portions that move relative to one another when said stent moves between its collapsed and expanded states. The said restraining member comprises a sheet of material adapted to be wrapped around at least a portion of the stent when it is in its collapsed state, and portions of the sheet being adapted for coupling to one another to maintain said sheet wrapped around at least a portion of the stent in its collapsed state. The said assembly further includes a member having a first portion coupled to the restraining member and a second portion coupled to one of the stent first and second portions.

According to another aspect of the invention, an expandable stent, which is restrained in a collapsed state with a restraining member, is released and the restraining member urged against the wall of the lumen in which the stent is placed. Since the restraining member remains at the site, the number of deployment steps can be reduced as compared to other techniques (e.g. pushing a self-expanding implant out the end of a radially constraining sheath and retracting the sheath).

According to another aspect of the invention, a method of preparing a stent for delivery comprises restraining a collapsed stent in a sheet of material which may be in the form of a tube and coupling side margins of the tube.

According to another aspect of the invention, an expandable stent (or stent-graft) is collapsed into a generally cylindrical or tubular restraining by pulling the stent through a tapered member and into a tubular restraining member.

The above is a brief description of some deficiencies in the prior art and advantages of the present invention. Other features, advantages, and embodiments of the invention will be apparent to those skilled in the art from the following description, accompanying drawings, and appended claims.

BRIEF DESCRIPTION OF THE DRAWINGS

FIG. 3 is a perspective view of the assembly of FIG. 1 with the restraint released and the implant in an expanded state.

FIG. 4A is an end view of the assembly of FIG. 3.

FIG. 4B is a bottom plan view of the restraining member of FIG. 4A.

FIGS. 8A, 8B, 8C, 8D, 8E and 8F diagrammatically show a procedure for loading an expandable stent-graft into a restraining member in accordance with the present invention prior to endolumenal delivery.

FIG. 9A diagrammatically shows delivering a restrained implant to a desired site in a mammalian body lumen in accordance with the present invention with the coupling member configured as shown in FIGS. 7A–7C.

FIG. 9B is a sectional view of FIG. 9A taken along line 9B—9B.

FIG. 9C shows an alternate multiple restraining member arrangement for that shown in FIG. 9A.

FIG. 10A diagrammatically shows partial deployment of the implant assembly illustrated in FIG. 9A showing progressive expansion in a direction away from the distal end of the illustrated guidewire (i.e., toward the illustrated hub).

FIG. 10B is a sectional view of FIG. 10A taken along line 10B—10B.

FIG. 11A diagrammatically shows full deployment of the implant assembly illustrated in FIG. 9A.

FIG. 11B is a sectional view of the implant assemby shown in FIG. 11A taken along line 11B—11B.

FIG. 14A is a perspective view of a bifurcated stent-graft that can be used with the illustrated delivery systems.

FIG. 26A is a front view of preassembled graft components.

FIGS. 26B and 26C are respectively the front view and top view of the assembled graft of FIG. 26A.

DETAILED DESCRIPTION

Figure 1:
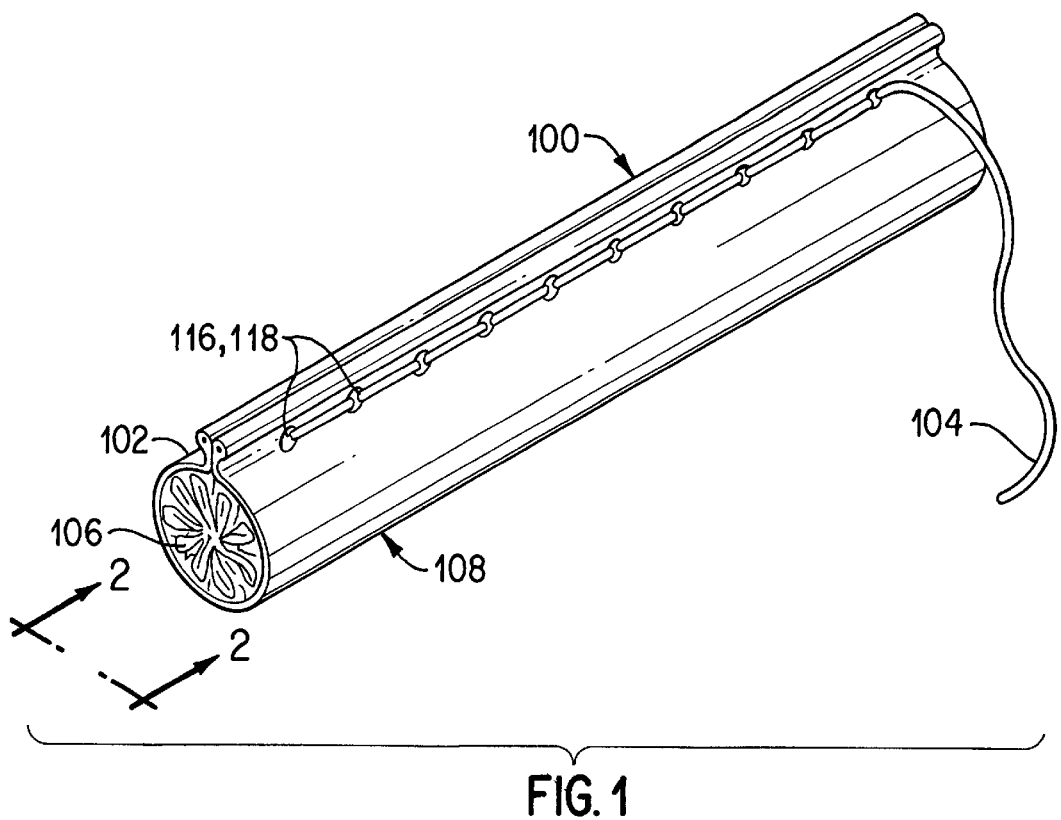
FIG. 1 is a perspective view of a mammalian implant that is restrained in a collapsed state in accordance with the principles of this invention.

Referring to the drawings in detail wherein like numerals indicate like elements, delivery systems for delivering implants or devices, such as stents or stent-grafts, to a desired site in mammalian vasculature are shown in accordance with the principles of the present invention. The delivery systems of the present invention generally include a restraining member that is adapted and configured for surrounding at least a portion of a collapsed or compressed implant and a coupling member(s) for releasably coupling portions of the restraining member to one another to maintain the implant in its collapsed or compressed state.

Figure 2:
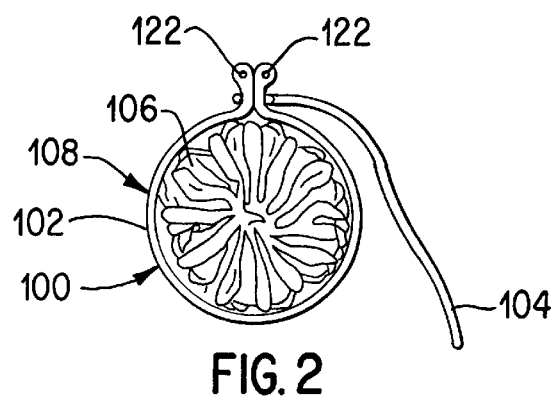
FIG. 2 is an end view of the restrained implant of FIG. 1.

Referring to FIGS. 1–4, an implant delivery system constructed in accordance with the present invention is shown. Delivery system (100), generally includes a restraining member (102), which as shown may be in the form of a sheet of material, and a coupling member (104) for releasably coupling portions of the restraining member to one another. The restraining member portions that are coupled may differ from those illustrated, but preferably are selected to maintain the implant, such as self-expanding stent-graft (106), in a collapsed or compressed state as shown in FIGS. 1 and 2 where the restraining member (102) is shown in the form of a tube. In the illustrative embodiment, the coupling member (104) is shown as a filament or thread-like element which prevents the restraining member (102) from rearranging to a configuration where the stent-graft (106) could expand to its expanded state.

The implant may be collapsed in any suitable manner for placement within the restraining member (102). For example, the implant may be folded or radially crushed before placement within the restraining member (102) as will be described in more detail below. As shown in FIGS. 9–11, a delivery assembly (108), which includes the restraining member (102) and the stent-graft (106), has relatively small cross-sectional dimensions which facilitate endoluminal delivery of the assembly to a site where the natural lumen diameter may be smaller than the expanded diameter of the stent-graft (106).

Referring to FIGS. 3 and 4A, stent graft (106) and restraining member (102) are shown in a deployed state after removal of the coupling member (104). The restraining member (102) may be fixedly secured to the stent-graft (106) so that the two components remain attached after expansion at the desired deployment site. The attachment between the restraining member and the stent-graft preferably is made to prevent significant movement between the restraining member and stent-graft after deployment which could disrupt endovascular fluid flow. Referring to FIGS. 4A and 4B multiple sutures (110) may be used to fixedly attach the restraining member (102) to the stent-graft (106). More specifically, the sutures can form loops that pass through the restraining member and around portions of the stent as shown in FIG. 4A. It is further noted that although one arrangement of the sutures (110) is shown in FIG. 4B other arrangements may be used.

Although other configurations of the restraining member (102) can be used, a preferred configuration is a generally rectangular one having constant width as shown in FIG. 4B. For example, in the case where the restraining member is used in conjunction with a modular bifurcated stent as will be described below, the restraining member may have a similar rectangular configuration as that shown in FIG. 4B. Alternatively, it may have two differently sized rectangular portions arranged to mate with the regions of different diameter (trunk and leg) or another configuration that would maintain the implant in a collapsed state when secured. Returning to FIG. 4B, the restraining member may be described as having side margins (112) that extend between the ends (114) of the member. Eyelets (116) are disposed along the side margins so that the coupling member (104) may be laced or threaded therethrough. The eyelets may be in the form of through holes (118), which may be formed by a uniform-diameter puncturing device or by other means such as laser-drilling. Alternatively, the eyelets may be formed by loops (120) which may be attached to the side margins (112) or formed by other means as would be apparent to one of ordinary skill in the art.

It is further desirable to have structural reinforcement at the side margins (112) to minimize or eliminate the possibility of the coupling member (104) from tearing the restraining member (102) when under load. Reinforced side margins may be formed by folding a portion of the restraining member (102) over a reinforcement member (122), such as a small diameter suture, which may be heat bonded between the two layers of sheet material. With this construction, a relatively low profile bead of material along the side margins (112) prevents or minimizes the possibility of tear propagation and, thus, accidental uncoupling of the restraining member (102). The small diameter suture (122) may comprise ePTFE, for example.

As the restraining member (102) constrains a collapsed self-expanding stent-graft, for example, forces resulting from stored spring energy in the collapsed stent-graft (106) will be acting on the restraining member (102) when it is configured for delivery. Thus, according to another aspect of the invention the restraining member (102) may comprise a material which is creep resistant and can withstand required loads without stretching over time. The restraining member (102) may comprise, for example, ePTFE, which is believed to provide suitable creep resistance, flexibility, and biocompatibility in a thin sheet form which can be heat bonded. Other materials also may be used including polyethers such as polyethylene terepthalate (DACRON® or MYLAR®) or polyaramids such as KEVLAR®.

The thread-like coupling member (104) may also comprise ePTFE. Sutures of polyethers such as polyethylene terepthalate (DACRON® or MYLAR®) or polyaramids such as KEVLAR® or metal wire comprising nitinol, stainless steel or gold may also be used for the coupling member (104). The coupling member (104) may simply extend to form a remote pull line as will be discussed below. Alternatively, a metallic pull line, such as one comprising stainless steel may be coupled to a nonmetallic coupling member (104) such as one comprising ePTFE. The coupling may be made by folding the end of the metallic pull line back upon itself to form an eyelet and threading the coupling member therethrough and securing it to the eyelet with a knot.

It is further noted that the width of the restraining member, when in a flat orientation as shown in FIG. 4A, preferably is less than the diameter of the implant. Typically the restraining member width will be less than about 40 mm (typically about 25–40 mm when the device is sized for thoracic aorta applications), and typically less than about 15 mm in other applications where the lumen is smaller. The sheet of material preferably has a thickness less than 0.010 inch (0.254 mm) and more preferably less than 0.005 inch (0.127 mm). In addition, the length of the restraining member preferably is less than or equal to that of the implant.

According to the present invention, a retraction assembly may be provided to retract the restraining member during expansion of the implant, so that the length of the restraining member is maintained to be about equal to or less than that of the implant. The expandable portion of the implant may undergo minor amounts of shortening along the axial direction due to the expansion thereof in the radial direction, which may lead to an overlap of the restraining member at the ends of the implant, but for the use of some type of retraction assembly in these situations. The retraction assembly minimizes or eliminates the risk of the restraining member extending beyond the implant and interfering with any channel formed by the implant, or any fluid flowing therethrough after expansion.

Figures 5A, 5B:
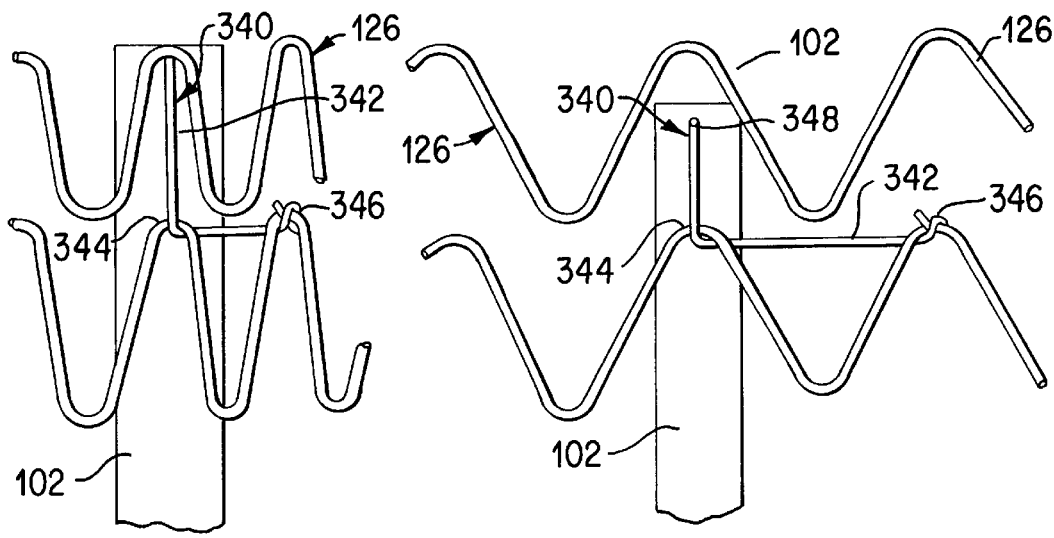
FIG. 5A shows a restraining member retraction mechanism according to another embodiment of the invention where the mechanism is in an unactuated state.
FIG. 5B shows the mechanism of FIG. 5A in an actuated state.

Referring to FIGS. 5A–5D, retraction assemblies or mechanisms constructed according to the principles of the invention are shown. In FIG. 5A, a retraction assembly (340) is shown including a biocompatible filament (342), which includes a portion that is stitched, tied or otherwise fixed to the restraining member (102), as shown at an attachment point (348), adjacent to one end of the restraining member. Filament (342) is passed underneath the members forming the first or end helical turn of the stent (126) and looped under or otherwise slidably secured to a portion of the second, third or another helical turn other than the first helical turn such as an apex or bend portion (344) in a second turn. The other end portion of filament (342) is further fixed, by tying or other means, to a portion of the stent that is circumferentially spaced from the attachment point (348) or the apex or bend portion (344), for example, such as an apex or bend portion (346) of the same helical turn. Preferably, the filament (342) is looped through an apex portion (344) of the second helical turn and tied to an apex portion (346) which is adjacent to the apex portion (344) as shown in FIG. 5A.

FIG. 5A shows the stent in the compressed state. Upon expansion of the stent, as mentioned above, the members of the stent expand to effect the radial expansion of the stent, as shown in FIG. 5B. Because the distance between apex portions (344) and (346) becomes greater upon expansion of the stent, and because the filament (342) is relatively unyieldable and inelastic, the distance between the attachment point (348) and the apex portion (344) necessarily decreases. The result is that the end of the restraining member (102) is retracted with respect to the stent (126), as shown in FIG. 5B. Thus, the retraction along the longitudinal axis of the restraining member is driven by the expanding distance between adjacent apexes in this embodiment. Although only one retraction mechanism is shown at one end of the restraining member, another similarly configured and arranged retraction mechanism may be used at the other end of the restraining member.

Figures 5C, 5D:
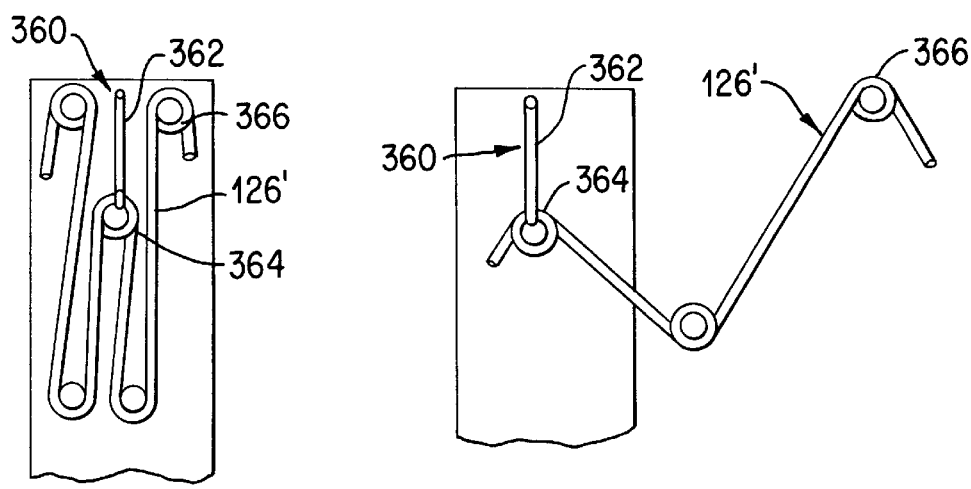
FIG. 5C shows a retraining member retraction mechanism according to yet another embodiment of the invention where the mechanism is in an unactuated state.
FIG. 5D shows the mechanism of FIG. 5C in an actuated state.

FIGS. 5C and 5D show another embodiment for a retraction assembly. The views of this assembly (as are those shown in FIGS. 5A and 5B) are taken from a location between the generally cylindrical graft and stent looking radially outward. In contrast to that shown above where one end portion of a filament is secured to the restraining member and another to a portion of the stent that circumferentially moves during stent expansion, the other end of the filament is secured to a portion of a stent that moves generally parallel to the longitudinal axis of the stent (axially) as the stent expands. In this embodiment, at least one apex portion (364) of an end helix of the stent member (126') (which differs from stent (126) in that it includes eyelets or loops which may be formed as shown in the drawings) is made shorter than the majority of apex portions (366). However, the apex portions may be otherwise configured such as those shown in FIGS. 5A and 5B A filament (362) is tied or otherwise fixed at one end to apex portion (364), and at the other end, to one end portion of the restraining member (102). As shown in FIG. 5D, upon radial expansion of the stent, inwardly positioned apex portion (364) retracts to a greater extent in the longitudinal or axial direction than the full height apex portions (366) which are shown in the last or most outwardly positioned turn of the stent. This relative greater retraction directly translates through filament (362) such that the end of the restraining member (102) is retracted relative to apex portions (366). As described above, another similarly constructed retraction mechanism may be provided at the other end of the restraining member.

Returning to FIG. 1, one stent-graft construction that may be used in conjunction with the delivery systems disclosed herein is shown. Stent-graft (106) generally includes a thin-walled tube or graft member (124), a stent member (126), which can be a self-expanding stent, and a ribbon or tape member (128) for coupling the stent (126) and graft (124) members together. The stent (126) and graft (124) members may be heat bonded together, thus sealing in portions of the stent member (126) that are between the tape member (128) and the graft member (124). The mechanical properties of the stent-graft (106) may be customized, for example, through materials selection, by varying the structural pattern of the stent member, varying the thickness of the tape (128) and graft (124) members, and varying the pattern with which the tape member contacts the stent and graft members.

As shown in FIG. 3, the tape member (128) may cover only a portion of the stent member (126) as it follows the helical turns of the undulating stent member. With this construction, regions of the stent member do not interface with the tape member when the stent-graft is in an uncompressed state, for example. This is believed to advantageously reduce shear stresses between the stent member (126) and the tape member (128) when the stent-graft undergoes bending or compression, thereby reducing the risk of tearing the graft (124) or tape (128) members or causing delamination between the stent (126) and graft (124) members.

The tape member (128) also preferably has a generally broad or flat surface for interfacing with the stent (126) and graft (124) members as compared to filament or thread-like structures such as sutures. This increases potential bonding surface area between the tape member (128) and the graft member (124) to enhance the structural integrity of the stent-graft. The increased bonding surface area also facilitates minimizing the thickness of the tape member (128). It has been found that a tape member in the form of a generally flat ribbon as shown in the drawings provides desired results.

Tape members having widths of 0.025, 0.050 and 0.075 inches applied to a stent member having a peak-to-peak undulation amplitude of about 0.075 inch are believed to provide suitable results. However, it has been found that as the tape member band width increases, the stent-graft flexibility generally is diminished. It is believed that a tape member width of about one-fourth to three-fourths the amplitude of the stent member undulations, measured peak-to-peak, may be preferred (may be more preferably about one-third to two-thirds that amplitude) to optimize flexibility. It also has been found that by positioning one of the lateral margins of the tape member adjacent to the apexes, the tape member width may be reduced without significantly sacrificing apex securement. Varying the width of the tape member (e.g., varying width of the tape along the length of the stent graft) can also result in the adjustment of other structural properties. Increasing the width can also potentially increase the radial stiffness and the burst pressure and decrease the porosity of the device. Increasing band width can also diminish graft member wrinkling between coupling member turns.

The tape member (or separate pieces thereof) also may surround the terminal end portions of the stent-graft to secure the terminal portions of the graft member to the stent member.

Figure 6A:
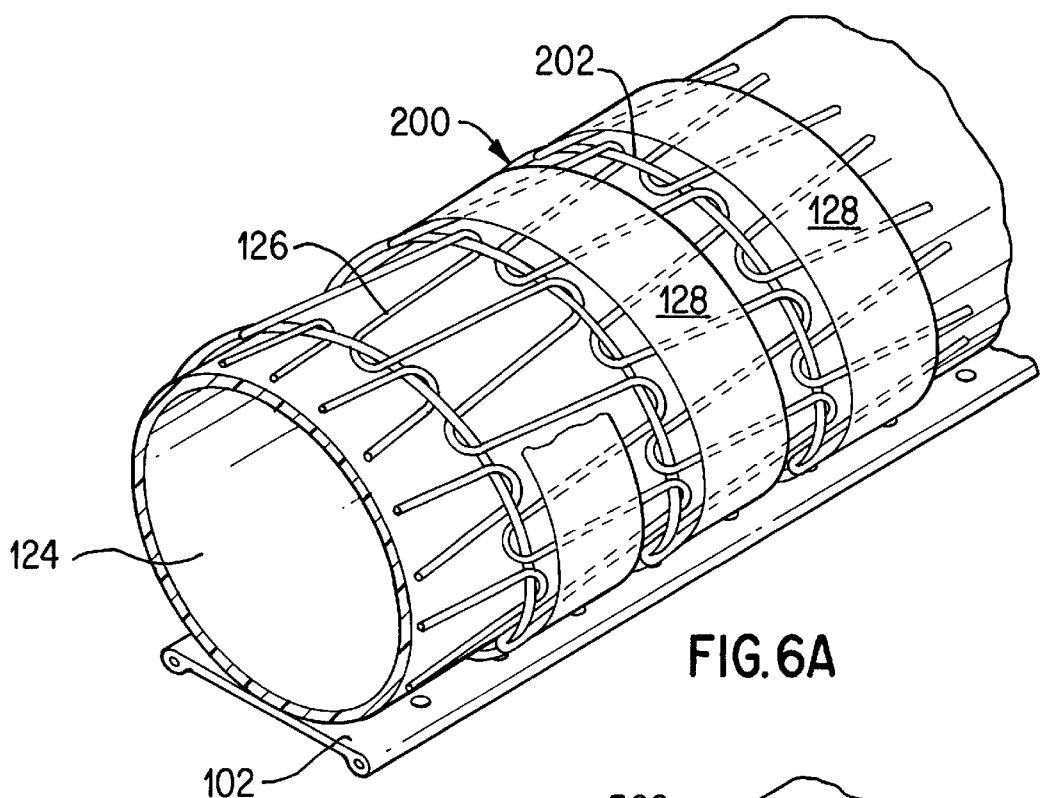
FIG. 6A is a perspective view of another embodiment of the implant in conjunction with the restraining member of FIG. 1.
Figure 6B:
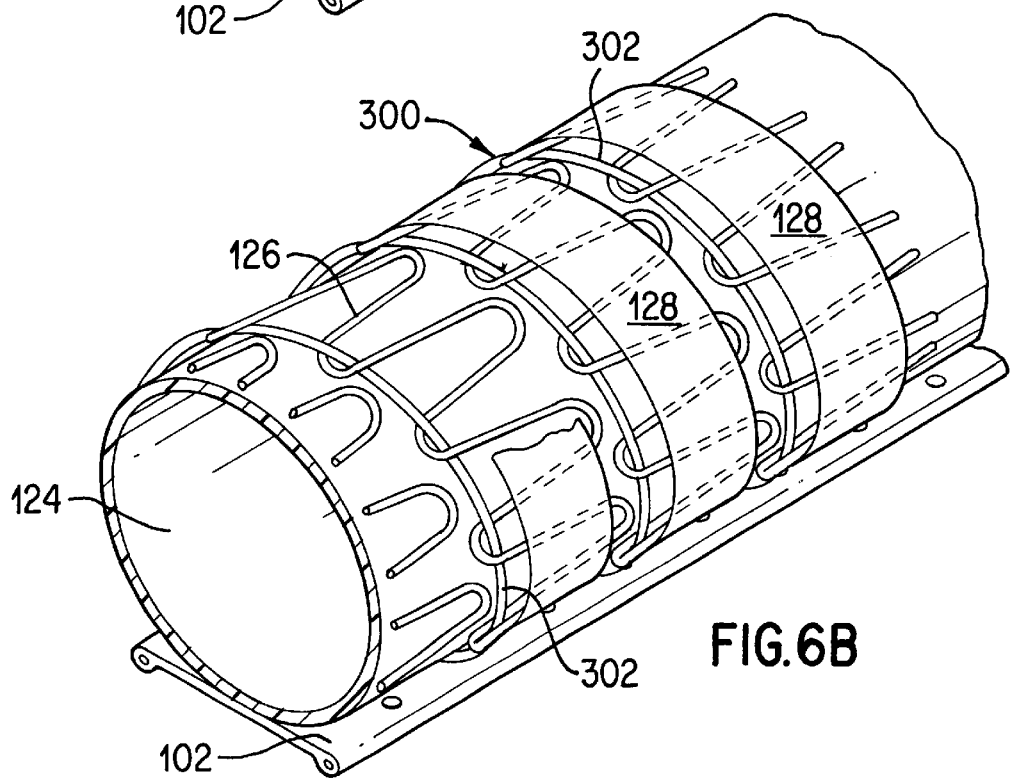
FIG. 6B is a perspective view of a further embodiment of the implant in conjunction with the restraining member of FIG. 1.

FIGS. 6A and 6B illustrate further stent-graft constructions that may be used with the delivery systems described herein. Referring to FIG. 6A, stent-graft (200) is the same as stent-graft (106) with the exception that stent-graft (200) includes a filament that couples stent undulations in adjacent turns. Filament (202) is laced or interwoven between undulations of the stent member and acquires a helical configuration (i.e., it forms a secondary helix) in being laced as such. Such a configuration is disclosed in PCT publication No. WO 95/26695 (International Application No. PCT/US95/04000) the entirety of which is hereby incorporated herein by reference. The stent-graft (300) shown in FIG. 6B is the same as that shown in FIG. 6A with the exception that the filament (302) is interwoven between undulations in the same helical turn of the stent member.

The filaments (202, 302) are of the same construction and may be of any appropriate filamentary material which is blood compatible or biocompatible and sufficiently flexible to allow the stent to flex and not deform the stent upon folding. Although the linkage may be a single or multiple strand wire (platinum, platinum/tungsten, gold, palladium, tantalum, stainless steel, etc.), much preferred is the use of polymeric biocompatible filaments. The flexible link may be tied-off at either end of the stent-graft (200, 300), for example, by wrapping its end portion around the stent and tying it off at the point at the beginning of the last turn as would be apparent to one of ordinary skill.

A percutaneously delivered stent-graft must expand from a reduced diameter, necessary for delivery, to a larger deployed diameter. The diameters of these devices obviously vary with the size of the body lumen into which they are placed. For instance, the stents of this invention may range in size from 2.0 mm in diameter (for neurological applications) to 40 mm in diameter (for placement in the aorta). A range of about 2.0 mm to 6.5 mm (perhaps to 10.0 mm) is believed to be desirable. Typically, expansion ratios of 2:1 or more are required. These stents are capable of expansion ratios of up to 5:1 for larger diameter stents. Typical expansion ratios for use with the stents-grafts of the invention typically are in the range of about 2:1 to about 4:1 although the invention is not so limited. The thickness of the stent materials obviously varies with the size (or diameter) of the stent and the ultimate required yield strength of the folded stent. These values are further dependent upon the selected materials of construction. Wire used in these variations are typically of stronger alloys, e.g., nitinol and stronger spring stainless steels, and have diameters of about 0.002 inches to 0.005 inches. For the larger stents, the appropriate diameter for the stent wire may be somewhat larger, e.g., 0.005 to 0.020 inches. For flat stock metallic stents, thicknesses of about 0.002 inches to 0.005 inches is usually sufficient. For the larger stents, the appropriate thickness for the stent flat stock may be somewhat thicker, e.g., 0.005 to 0.020 inches.

The following example is provided for purposes of illustrating a preferred method of manufacturing a stent-graft as shown in FIG. 3. It should be noted, however, that this example is not intended to limit the invention. The stent member wire is helically wound around a mandrel having pins positioned thereon so that the helical structure and undulations can be formed simultaneously. While still on the mandrel, the stent member is heated to about 460° F. for about 20 minutes so that it retains its shape. Wire sizes and materials may vary widely depending on the application. The following is an example construction for a stent-graft designed to accommodate a 6 mm diameter vessel lumen. The stent member comprises a nitinol wire (50.8 atomic % Ni) having a diameter of about 0.007 inch. In this example case, the wire is formed to have sinusoidal undulations, each having an amplitude measured peak-to-peak of about 0.100 inch and the helix is formed with a pitch of about 10 windings per inch. The inner diameter of the helix (when unconstrained) is about 6.8 mm. (The filament when used as shown in FIGS. 6A and 6B may have a diameter of about 0.006 inch.)

In this example, the graft member is porous expanded polytetrafluorethylene (PTFE), while the tape member is expanded PTFE coated with FEP. The tape member is in the form of a flat ribbon (as shown in the illustrative embodiments) that is positioned around the stent and graft member as shown in FIG. 3. The side of the tape member or ribbon that is FEP coated faces the graft member to secure it to the graft member. The intermediate stent-graft construction is heated to allow the materials of the tape and graft member to merge and self-bind as will be described in more detail below.

The FEP-coated porous expanded PTFE film used to form the tape member preferably is made by a process which comprises the steps of:

(a) contacting a porous PTFE film with another layer which is preferably a film of FEP or alternatively of another thermoplastic polymer;

(b) heating the composition obtained in step (a) to a temperature above the melting point of the thermoplastic polymer;

(c) stretching the heated composition of step (b) while maintaining the temperature above the melting point of the thermoplastic polymer; and (d) cooling the product of step (c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching.

In constructing this example, the thin wall expanded PTFE graft was of about 0.1 mm (0.004 in) thickness and had a density of about 0.5 g/cc. The microstructure of the porous expanded PTFE contained fibrils of about 25 micron length. A 3 cm length of this graft material was placed on a mandrel having the same diameter as the inner diameter of the graft. The nitinol stent member having about a 3 cm length was then carefully fitted over the center of the thin wall graft.

The stent-member was then provided with a tape coupling member comprised of the FEP coated film as described above. The tape member was helically wrapped around the exterior surface of the stent-member as shown in FIG. 3. The tape member was oriented so that its FEP-coated side faced inward and contacted the exterior surface of the stent-member. This tape surface was exposed to the outward facing surface of the thin wall graft member exposed through the openings in the stent member. The uniaxially-oriented fibrils of the microstructure of the helically-wrapped ribbon were helically-oriented about the exterior stent surface.

The mandrel assembly was placed into an oven set at 315° C. for a period of 15 minutes after which the film-wrapped mandrel was removed from the oven and allowed to cool. Following cooling to approximately ambient temperature, the mandrel was removed from the resultant stent-graft. The amount of heat applied was adequate to melt the FEP-coating on the porous expanded PTFE film and thereby cause the graft and coupling members to adhere to each other. Thus, the graft member was adhesively bonded to the inner surface of the helically-wrapped tape member through the openings between the adjacent wires of the stent member. The combined thickness of the luminal and exterior coverings (graft and tape members) and the stent member was about 0.4 mm.

Although the invention has been described with reference to the stent-graft examples illustrated in the drawings, it should be understood that it can be used in conjunction with other devices, stents or stent-grafts having constructions different than those shown. For example, delivery systems described herein may be used in conjunction with bifurcated stents or stent-grafts as will be described in detail below. In addition, although a self-expanding stent-graft has been described, balloon expanding stent-grafts also may be used in conjunction with the delivery systems described herein. These stent-grafts require a balloon to expand them into their expanded state as opposed to the spring energy stored in a collapsed self-expanding stent.

Figure 7A:
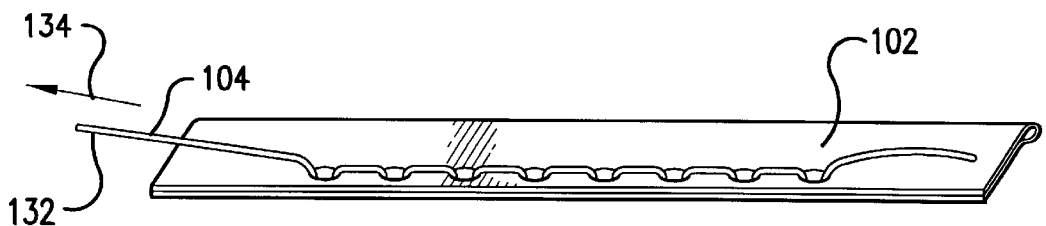
FIG. 7A illustrates the restraining and coupling member of FIG. 1 and the pull direction for removing the coupling member from the restraining member.
Figure 7B:
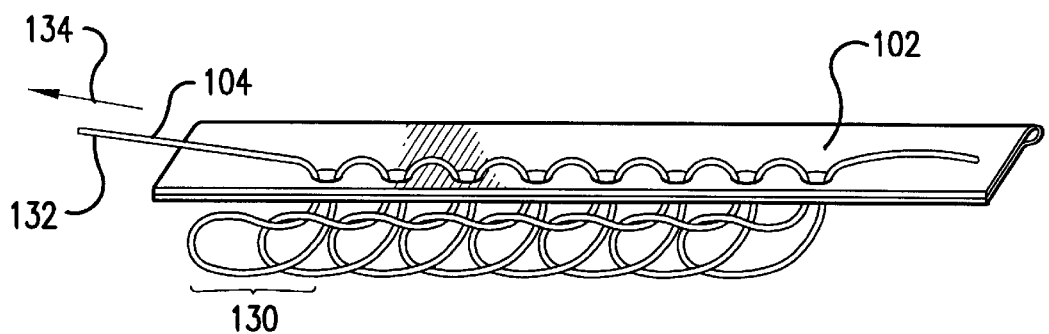
FIG. 7B shows the assembly of FIG. 7A with the coupling member loosened to illustrate the chain knots used according to one embodiment of the invention.
Figure 7C:
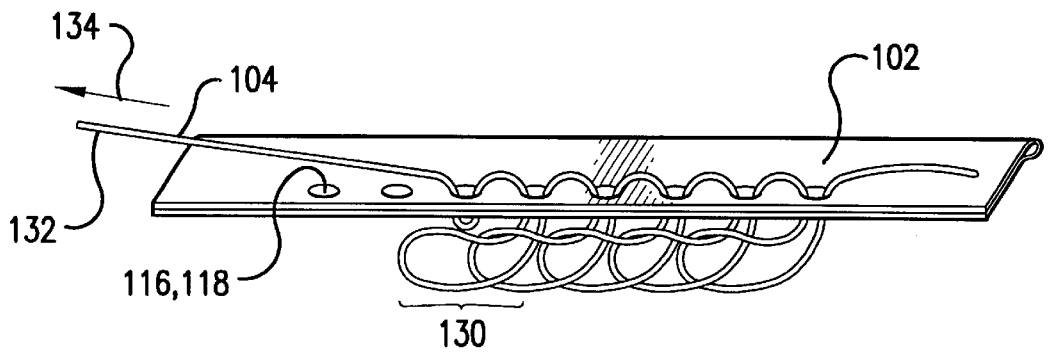
FIG. 7C diagrammatically represents release of the assembly of FIG. 7A or 7B as the coupling member is pulled in the direction shown.

Referring to FIGS. 7A–C, one slip knot configuration that may be used in conjunction with the thread-like coupling member (104) will be described. The restraining member (102) is shown without an implant positioned therein for purposes of simplification. FIG. 7A illustrates the slip knot in a prerelease or predeployment state. The series of knots are generally flush with the restraining member (102) surface and add very little profile to the construct which is preferred during implant delivery. FIG. 7B shows the assembly of FIG. 7A with the thread-like coupling member (104) loosened to illustrate how the chain knots (130) may be formed. FIG. 7C diagrammatically represents release of the assembly of FIG. 7A or 7B. The illustrated stitch is releasable by pulling one end of the line that results in releasing of the cylindrical or tubular restraining member and then deployment of the device. This particular stitch is called a chain stitch and may be created with a single needle and a single line. A chain stitch is a series of loops or slip knots that are looped through one another such that one slip knot prevents the next slip knot from releasing. When the line is pulled to release a slip knot, the following slip knot is then released and that releases the next slip knot. This process continues during pulling of the line until the entire line is pulled out of the restraining member.

Referring to FIGS. 7A–C, as the unknotted portion or the lead (132) of the thread-like coupling member (104) is pulled, such as in the direction shown by reference arrow (134), each consecutive chain knot (130) releases the next adjacent one. In the preferred embodiment, the chain knots (130) of the coupling member (104) are arranged to progressively release the collapsed implant in a direction away from the distal portion of the delivery catheter as shown in FIG. 10A and as will be discussed in detail below.

Figure 8A:
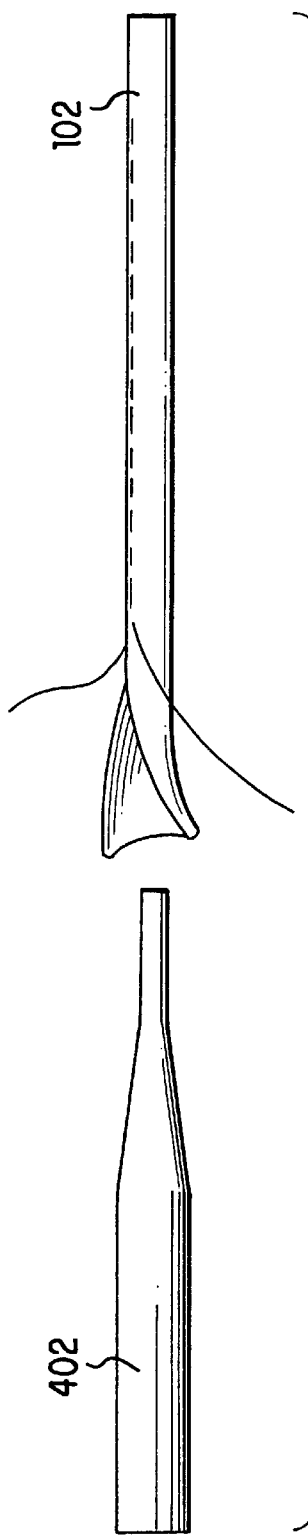
Figure 8B:
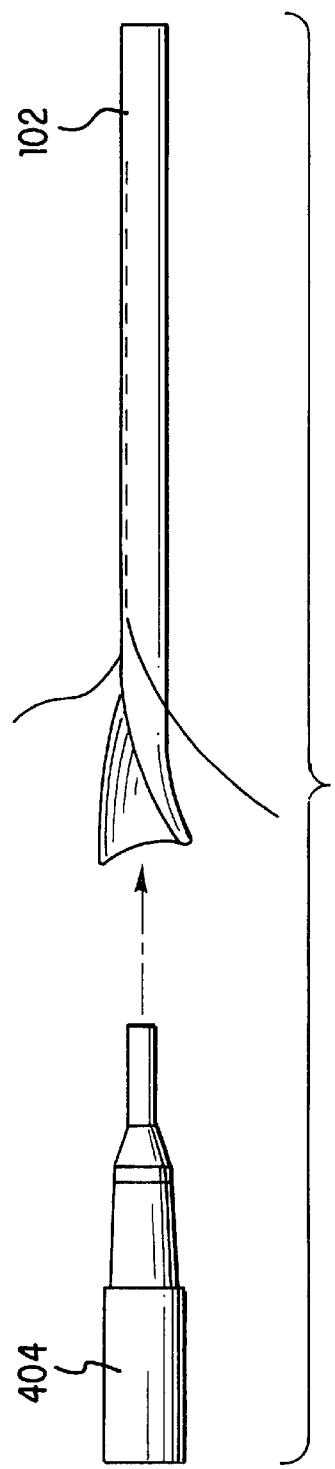
Figure 8C:
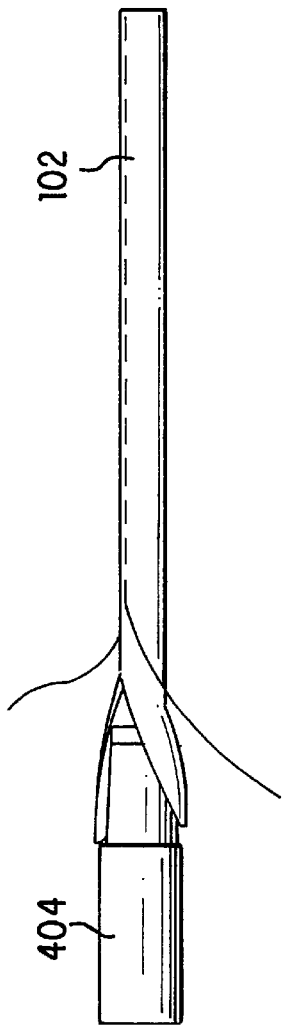

Referring to FIGS. 8A through 8F, a method for making an assembly comprising a restraining member with a collapsed or compressed implant therein is shown for purposes of example. FIG. 8A shows the restraining member (102) with its side margins releasably coupled to one another and its left end dilated by a tapered mechanical dilator (402). A small funnel (404) is then inserted into the restraining member (102) as shown in FIGS. 8B and 8C. The small funnel (404) and restraining member (102) are then mounted onto a pulling frame (410), and a large funnel (406) is fitted into the small funnel (404) as shown in FIG. 8D. Traction or pull lines (408), which have been sutured to one end of the stent-graft, (106) are pulled through the large funnel (406), small funnel (404), and restraining member (102) with a tapered mandrel (416). As shown in FIGS. 8F, the pull lines (408) are fastened to a tie down post (412) located on a tension screw (414) and then are pulled by the tension screw (414). The stent-graft (106) is then pulled and collapsed sequentially through the large (406) and small (404) funnels, and then into the restraining member (102). Once the stent-graft (106) has been radially collapsed into the restraining member (102), which has its side margins coupled together, the pull lines (408) can be removed. The mandrel (416) may be inserted into the restrained implant to facilitate introduction of another component. In the preferred embodiment, a multilumen catheter (136) (FIGS. 9–11) is introduced through the center of the compressed stent-graft (106) and is used to deliver the radially restrained stent-graft to the desired endoluminal site.

It also is noted that the funnels may be chilled to facilitate compression of the stent when the stent is made of nitinol. That is, when the stent is made of nitinol, the funnels may be chilled below 0° C. or below the transition temperature (Mf) where nitinol is in its martensitic state. In addition, the stent-graft could be folded first and then reduced in profile by pulling through the funnel and into the restraining member. Cooling may be accomplished by spray soaking the stent-graft with chilled gas such as tetrafluoroethane. Micro-Dust™ dry circuit duster manufactured by MicroCare Corporation (Conn) provides suitable results. The spray canister preferably is held upside down to discharge the fluid as a liquid onto the stent-graft.

A method of deploying an implant will be described with reference to FIGS. 9–11. In general, an implant may be delivered percutaneously with the delivery systems described herein, typically through the vasculature, after having been assembled in the reduced diameter form (see e.g. FIG. 1). At the desired delivery site, the implant may be released from the restraining member, thus allowing the implant to expand or be expanded against the lumen wall at the delivery site. Although other devices including stents or stent-grafts may be used, such as balloon expandable stents, the following example will be made with reference to a self-expanding stent-graft, which has the ability to fully expand itself into its final predetermined geometry when unconstrained. More particularly, the following example will be made using a delivery system as shown in FIGS. 1 and 7A–C and a stent-graft construction as shown in FIG. 3.

Referring to FIGS. 9A and 9B, an implant delivery assembly including a collapsed stent-graft (106) that is confined within a restraining member (102) and, which surrounds a distal portion of the multilumen delivery catheter (136), is shown. The attending physician will select a device having an appropriate size. Typically, the stent-graft will be selected to have an expanded diameter of up to about 20% greater than the diameter of the lumen at the desired deployment site.

The delivery catheter preferably is a multilumen catheter. The proximal portion of the catheter (136) is coupled to a hub (140), which includes a guidewire port (142) for a guidewire (143), and a deployment knob (144), which is coupled to the lead (132) of the thread-like coupling member (104). Accordingly, when the knob (144) is retracted, the restraining member (102) is released so that the stent-graft may expand. The hub (140) also may include a flushing port (146) as is conventional in the art. The stent-graft (106) is held axially in place prior to deployment by a proximal barrier (148) and distal barrier (150) which are positioned around multilumen delivery catheter (136) adjacent to the proximal and distal portions, respectively, of the restrained stent-graft. The proximal and distal barriers (148, 150) may be fixedly secured to the multilumen delivery catheter (136) to restrict any axial movement of the restrained stent-graft. The barriers preferably are positioned to abut against the stent-graft or restraining member. The lead (132) of the coupling member (104) is passed through an aperture (152) in the proximal barrier (148) which is fluidly coupled to a lumen in the multilumen delivery catheter (136) so that the coupling member lead (132) can be coupled to the deployment knob (144). FIGS. 9A and 9B show advancement of the catheter (136) and the restrained implant through a vessel (154) toward a desired site. Referring to FIGS. 10A and 10B, once the restrained stent-graft reaches the desired site (156), the deployment knob (144) is retracted so that the stent-graft progressively expands as shown in the drawings as the coupling member (104) is removed from the restraining member. The coupling member preferably is arranged to facilitate stent-graft expansion in a direction from the distal to proximal ends of the stent-graft (i.e., in a direction from the catheter tip to the catheter hub). FIGS. 11A and 11B show the stent-graft (106) and restraining member (102) in their final implantation position after the coupling member and catheter have been removed therefrom. In another embodiment, multiple restraining members may be used as shown in FIG. 9C. When the multiple coupling members (104) are released simultaneously implant deployment time may be reduced.

A method for deploying a balloon expandable stent-graft may be the same as that described above, with exception that after the coupling member (104) has been retracted from the eyelets (116), the balloon, which may be positioned inside the stent-graft prior to delivery, is inflated to expand the stent-graft (106) and then deflated for removal through the catheter (136).

According to further embodiments of the invention, multidirectional coupling member release or multiple coupling members may be used. These configurations may facilitate more rapid deployment of the implant than when a single unidirectional coupling member is used. FIGS. 12A–12D diagrammatically show multidirectional deployment of a restrained implant according to the principles of the invention where a coupling member arrangement is provided to release the implant from its middle portion, preferably its axial center, outward toward the implant ends. Although a particular coupling member configuration is not shown in these diagrammatic representations, one suitable coupling configuration is shown in FIG. 13 where the leads (132) may be passed through the aperture (152) and coupled to the deployment knob (144) as shown in FIG. 9A and described above.

Figure 12A:
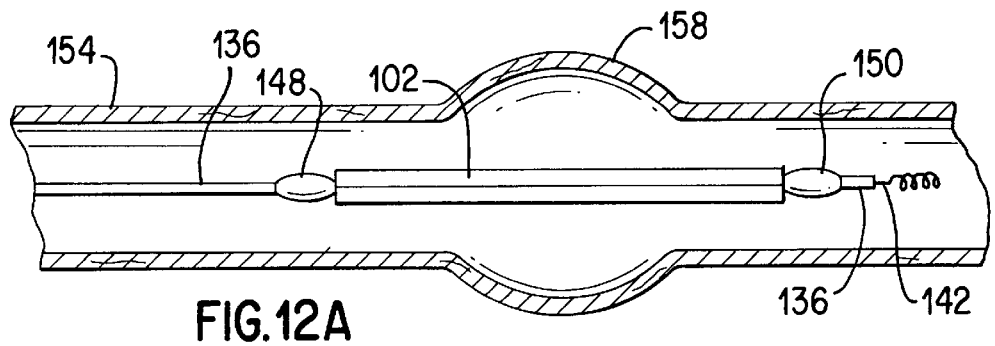
FIGS. 12A, 12B, 12C and 12D diagrammatically show deployment of a restrained implant according to another embodiment of the invention where the coupling member configuration provides release from the middle portion of the implant outward toward the implant ends.
Figure 12B:
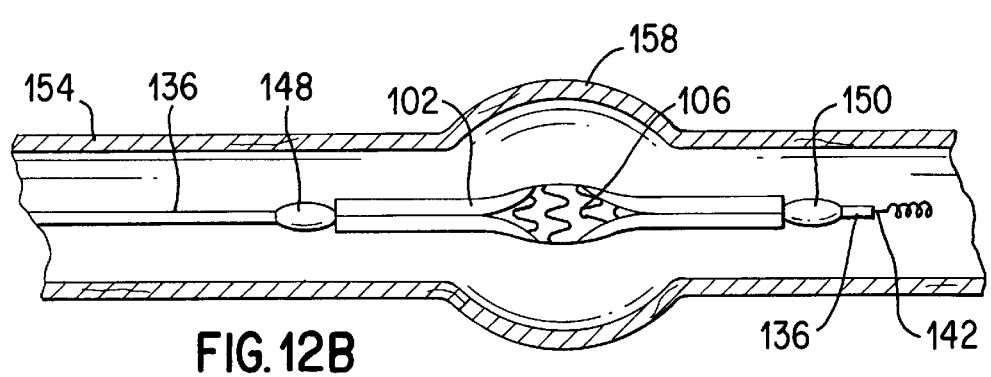
Figure 12C:
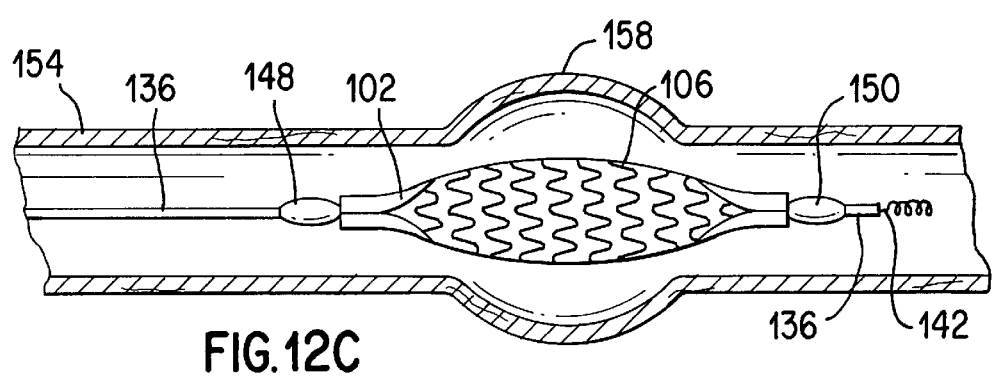
Figure 12D:
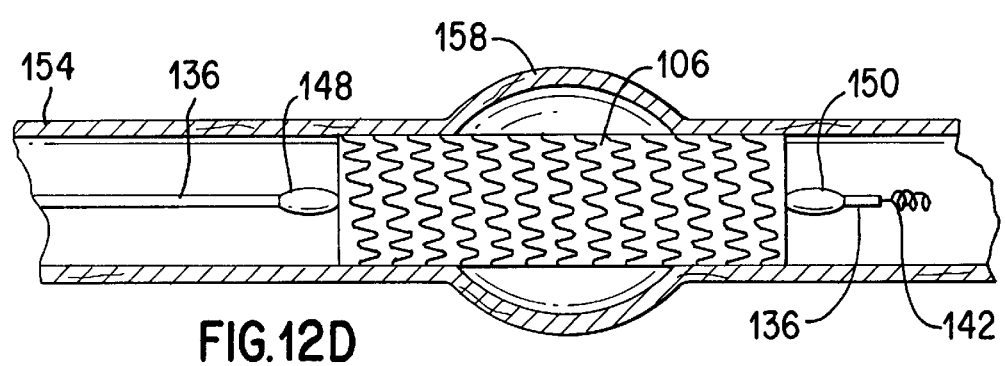

Referring to FIG. 12A, the restrained stent-graft, which is positioned on the distal end portion of delivery catheter (136), is advanced through a vessel (154) for deployment in an aneurysm (158). The axial midpoint of the restraining member (102) preferably is positioned at the center of the aneurysmal sac. As the coupling member arrangement unlacing propagates from middle of the construct toward the proximal and distal ends of the restraining member (102) and the stent-graft (106), the stent-graft (106) progressively expands from its axial midportion toward its ends as shown in FIGS. 12B and 12C. This may be accomplished by pulling the leads (132) shown in FIG. 13 simultaneously when the arrangement in that figure is used. The stent-graft size is selected so that when the restraining member is fully released and the stent-graft fully deployed as shown in FIG. 12D, the proximal and distal portions of the stent-graft are positioned against the proximal and distal necks of the aneurysm. The delivery catheter may then be retracted.

As is apparent from the drawings, this embodiment advantageously allows fluid flow through the aneurysmal sac to remain substantially unobstructed during the release of the restraining member. For example, the stent-graft ends are still constrained at the deployment time shown in FIG. 12C where the aneurysm neck regions are shown minimally obstructed. In addition, this simultaneous, multidirectional release of the restraining member advantageously reduces the time in which fluid flow in the vessel may disturb the implant position as it is deployed as compared to a single directional release mechanism such as that shown in FIGS. 9–11.

Figure 13:
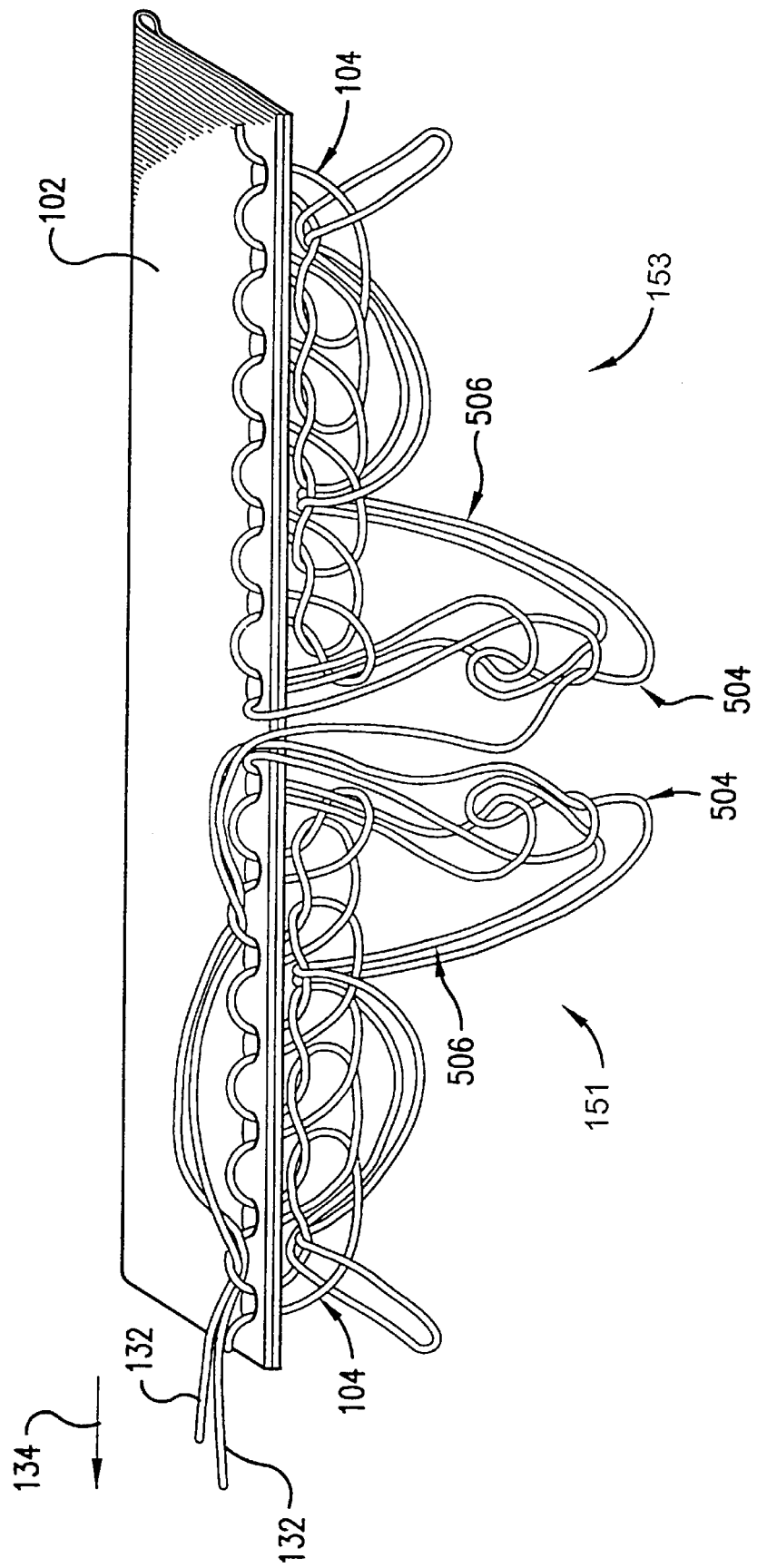
FIG. 13 illustrates one coupling member configuration for deployment as shown in FIGS. 12A–12D.

Referring to FIG. 13, a multiple coupling member configuration is shown. The illustrated arrangement includes two lacing configurations (151) and (153). Except for the placement of the lead (132) of thread-like coupling member (104), configuration (153) is the mirror image of configuration (151). Accordingly, description of only one of the configurations will be made for purposes of simplification. Referring to the lacing configuration (153), configuration (153) is the same as that shown in FIGS. 7A–C with the exception that configuration (153) further includes two additional slip knots, generally designated with reference numeral (504), and tuck or loop arrangement (506). The additional slip knots are not interwoven in the restraining member and provide a delay mechanism for release of the coupling member, as is apparent from the drawings, when the lead (132) is pulled in the direction of the arrow (134). Thus, inadvertent pulling of the lead (132) will not immediately begin to release the coupling member from the restraining member. The tuck arrangement simply involves tucking the slack from lead (132) under stitches at various intervals as shown so that the additional slip knots (504) may be pulled out of the way for delivery. In addition, the tuck or loop arrangement (506) provides an additional delay mechanism for release of the slip knots.

As discussed, the delivery systems described above can be used with other implants or devices. These systems, for example, can be used in conjunction with the bifurcated devices described below.

The modular stent-graft of FIGS. 14A through 14D generally has two principal components; a main body (700) and a contralateral leg (730) each generally having a graft member attached to a stent member according to the description above. The main body (700) generally has a number of sections which have distinct overall constructions. A distal trunk section (708) has a single lumen structure beginning at a distal end (702) of the main body (700) and continuing until a bifurcation point (728). The bifurcation point (728) is the location within the prosthesis where the single lumen of the distal trunk section (708) bifurcates into internal two flow lumen.

An intermediate section (710) begins at the bifurcation point (728) and continues to the receiving hole (704). In the intermediate section (710), the stent-graft has an internal graft structure which is bifurcated into two lumen surrounded by a generally tubular, single-lumen stent structure. Finally, a proximal section (712) is a single lumen structure for both the stent member and the graft member and includes an ipsalateral leg (726) which terminates at an ipsalateral leg hole (706).

The graft member of the intermediate section (710) bifurcates the single lumen distal trunk section (708) into the ipsalateral leg (726) and an internal female receiving lumen (703). The receiving lumen (703) terminates at a receiving hole (704). The receiving hole (704) and receiving lumen (703) accommodate delivery and attachment of the contralateral leg component (730). Preferably, the graft material at the distal end (734) of the contralateral leg component (730) is scalloped as shown more clearly in FIG. 23 discussed below.

The receiving hole (704) is supported by a wire structure around a substantial portion of its periphery so that the receiving hole (704) is held open after deployment. In a preferred embodiment the wire structure that supports the receiving hole (704) is an independent wire ring (714).

The independent wire ring (714) is located in the general area of the receiving hole (704) in the intermediate section (710). The independent wire ring (714) ensures that the graft material at the receiving hole (704) is supported in an open position to receive the distal end (734) of the contralateral leg (730). In absence of such support, the receiving hole (704) may not reliably open after delivery of the main body component (700) because within the intermediate section (710) the bifurcated graft member in the area of the receiving lumen (703) does not have full stent support on its interior periphery. This may be better seen in FIG. 18 which shows the absence of any internal stent support of the interior graft periphery (785) in the area of the receiving lumen (703).

The independent wire ring (714) may be comprised of the same materials as the other stent-graft sections discussed above and is preferably self-expanding. In a preferred embodiment, the independent wire ring comprises a single turn of an undulating wire stent material surrounded by at least one layer of tape which is heat bonded to the receiving hole (704). Alternatively, the independent wire ring (714) could be formed as the last turn of the main body (700).

A radiopaque marker may be used to make the receiving hole (704) visible during implantation. Such a marker may include a radiopaque wire adjacent to the independent wire ring (714). Such markers make it easier to see the location of the receiving hole (704) after deployment of the main body (700) within the mammalian body.

Figure 14B:
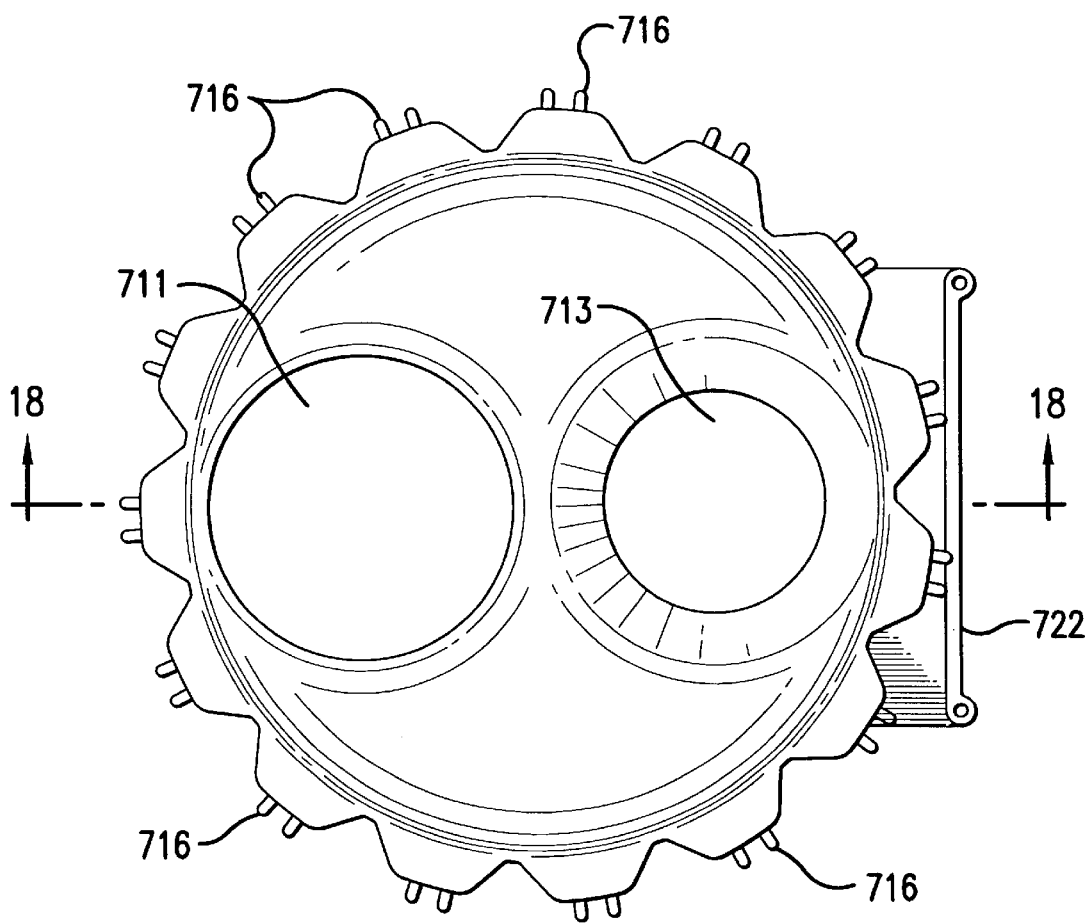
FIG. 14B is a top plan view of the bifurcated stent-graft of FIG. 14A.
Figure 14C:
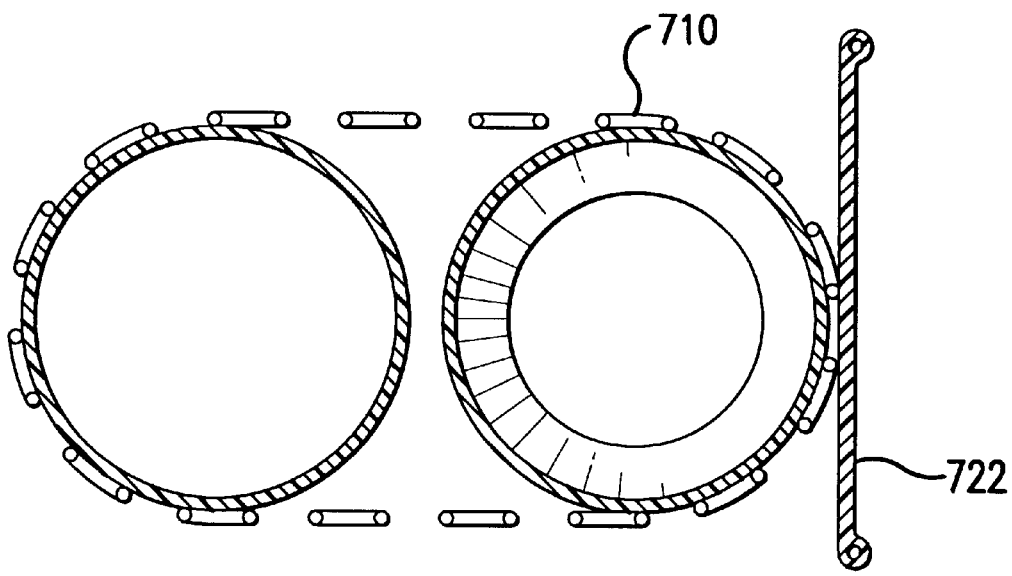
FIG. 14C is a cross-section view taken along section line 14C—14C depicted in FIG. 14A.

This construction of the intermediate stent section (710) as seen in cross-section in FIG. 14C is characterized by a single-lumen stent member and bifurcated graft member and offers both a smaller compressed profile as well as simplified manufacturing over constructions which have discreet stented leg features. The compressed profile is determined largely by the physical amount of stent and graft material present in a given section. This construction eliminates the stent material that would normally support the inside periphery of the bifurcated graft section resulting in less stent material to compress in that region. As the main body component (700) is compressed for delivery as discussed above, the compressed profile is significantly smaller than would be a structure that had a section of bifurcated stent over the section of bifurcated graft.

Even though bifurcated flow is supported, manufacturing is simplified because there is no bifurcated stent section. Winding a bifurcated stent section in one piece, for example, is a more complex process. Likewise, winding separate cylindrical stent structures and connecting them to form a bifurcated stent structure is complicated and ultimately may be less reliable. The intermediate section (710) allows the entire stent member that covers the main body component (700) to be made from a single undulating wire arranged in multiple helical turns. The result is a bifurcated stent-graft device which is simple to manufacture, easily compressible and which expands reliably upon deployment.

Figure 14D:
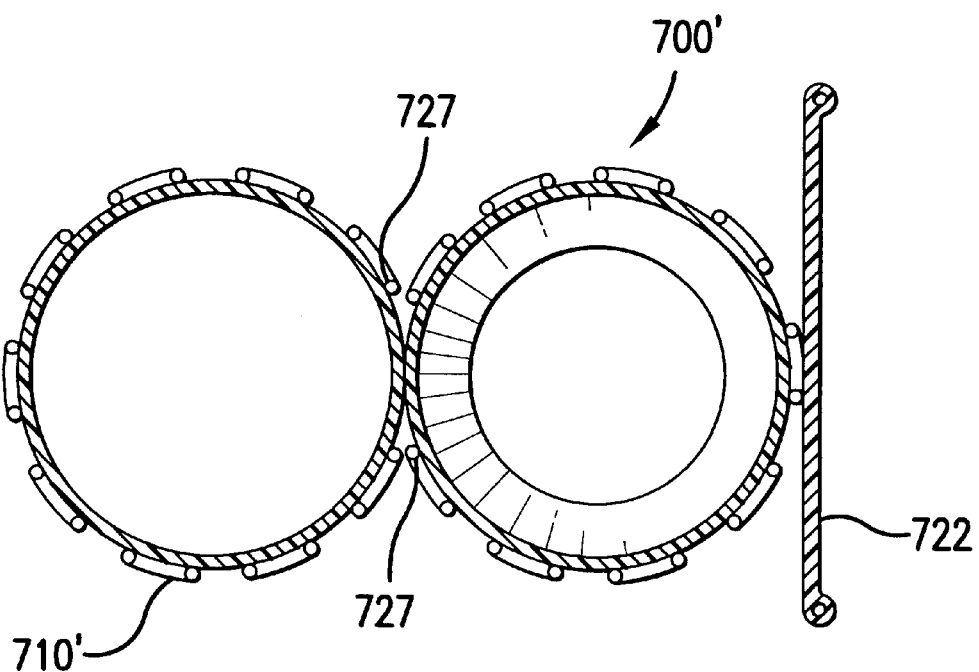
FIG. 14D is a cross-sectional view taken along section line 14D—14D depicted in FIG. 14A showing an alternate embodiment.

An alternate construction of the intermediate stent section (710), is shown in FIG. 14D. The intermediate stent section (710') has a shape characterized by the indented regions (727). The shape could generally be described as a 'figure-8', except that the area between the bifurcated graft member remains unsupported at its centermost region. This construction is still a single lumen stent construction and therefore maintains much of the benefits of reduced profile and simplified manufacturability while providing the bifurcated graft member with increased support around a greater portion of its perimeter. Further, indented portions (727) have less of a tendency to spring outward upon application of external forces.

As mentioned above, the main body component (700) and the contralateral leg component (730) are adapted for delivery in a compressed state to a bifurcation site within a body. For this purpose the main body component (700) is preferably equipped with a restraining member (722) constructed as described above. Likewise, the contralateral leg component (730) has an attached restraining member (732). These restraining members are typically sutured to the graft material at intervals down their length.

Figure 15:
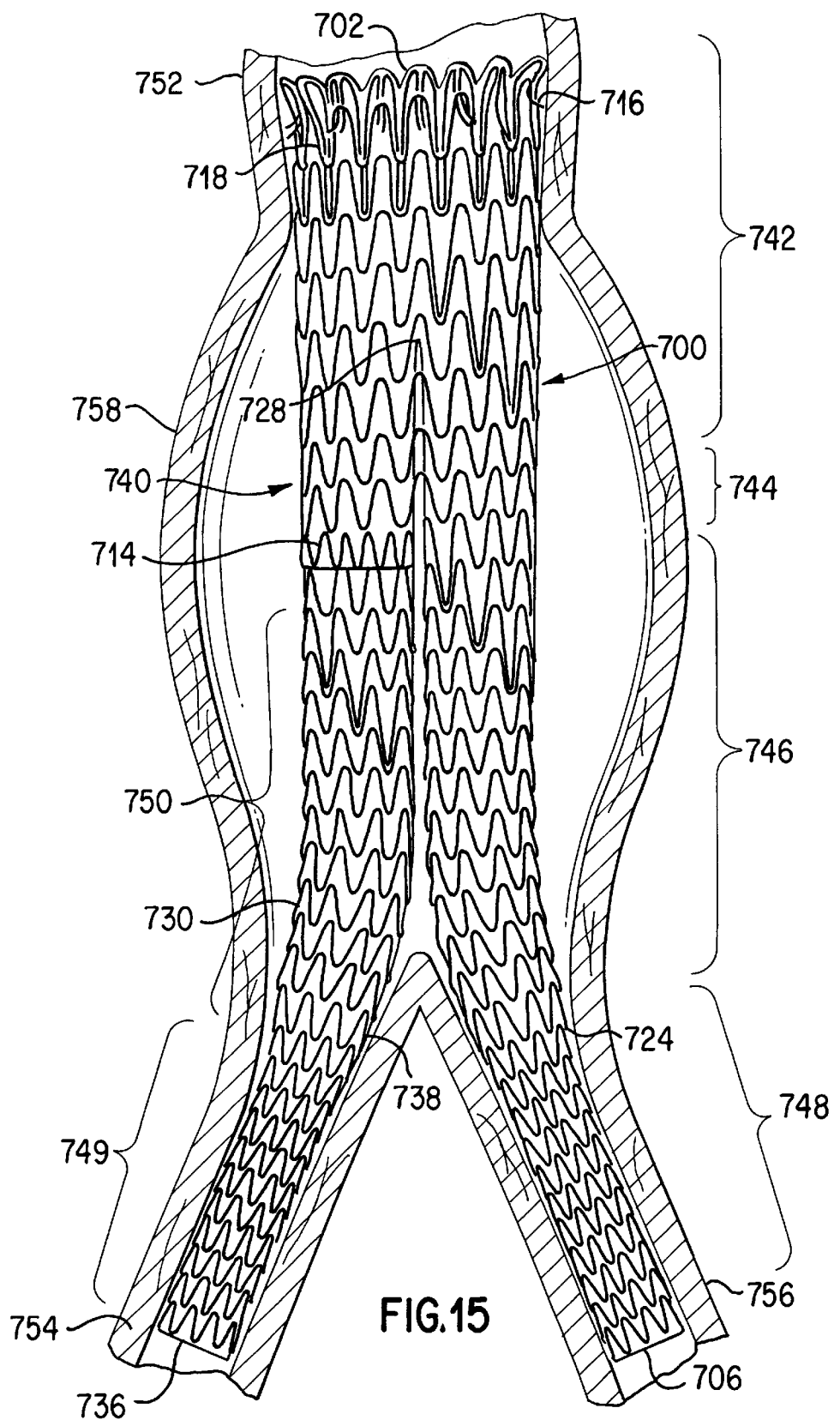
FIG. 15 is a front view of the assembled bifurcated stent-graft of FIG. 14A placed at a bifurcation site within the vasculature of a body.

FIG. 15 shows an assembled bifurcated stent-graft (740) after deployment at a bifurcation site within a bifurcated body vessel afflicted with an aneurysm (758). The prosthesis may be positioned at the location where the abdominal aortic artery (752) bifurcates into the left iliac artery (756) and the right iliac artery (754) as shown. So that the various features of the implant are more clearly shown, the restraining member is not shown in FIG. 15.

The assembled bifurcated stent-graft (740) is comprised of the main body component (700) and the contralateral leg component (730). The distal end (734) of the contralateral leg component (730) has been inserted into the receiving leg hole (704) and the female receiving lumen (703) of the main body component (700).

For best results in deploying any stent or stent-graft of these types it is essential that they have the appropriate structural properties such as axial stiffness, flexibility and kink-resistance. With complicated structures, such as those required for treating a bifurcated site, it is increasingly difficult to obtain the desired structural properties because optimizing one may negatively effect the other.

For instance, optimizing the global axial stiffness of a stent or stent-graft will necessarily make the device significantly less flexible and consequently impair its resistance to kinking and lessen its ability to conform to the natural bends or curves the body's vasculature. Conversely a device that has high flexibility with little axial stiffness is difficult to properly deploy and does not aid in anchoring the device in the desired location.

With these constraints in mind, it has been discovered that having a bifurcated stent-graft which has segments constructed with varying structural properties offers improved deployability, is less susceptible to kinking, and favorably tends to maintain its desired position after deployment while allowing sufficient flexibility to accommodate movement by the body. The exact structural properties desired may depend on the location where the prosthesis is to be deployed.

For these reasons, it is preferable that the bifurcated stent or stent-graft be constructed with at least two segments having structural properties different from one another. For example, in FIG. 14A, a length of the distal section (708) and the intermediate section (710) may be constructed with a higher axial stiffness for improved deployment and positional stability while the proximal section (712) may be constructed to have higher flexibility to accommodate the geometry of the iliac artery.

It may be further desirable to have a number of segments that have different structural properties. Accordingly, the main body component (700) and the contralateral leg component (730) of the assembled stent-graft (740) have segments constructed with structural properties different from adjacent segments. In one preferred embodiment shown in FIG. 15, the main body component (700) has four different segments constructed with different structural properties. The distal segment (742) is constructed to have higher axial stiffness than the more flexible proximally adjacent segment (744). The proximal section (748) is constructed to have a higher flexibility than that of its distally adjacent segment (746). Likewise the contralateral leg component (730) has an axially stiffer distal segment (750) and a more flexible proximal segment (749).

There are a number of ways to alter the structural properties of stent or stent-graft components. One way of selectively altering the structural properties of a stent-graft segment is to use a tape member for that segment that has different physical dimensions. Such a tape member is discussed above with reference to the tape member (128) of FIG. 3. For example the tape member width, thickness or spacing may be increased, from the preferred dimensions discussed above, in a segment where it is desirable to have increased or decreased stiffness. For example, the use of wider tape wound with closer spacing will increase the stiffness in that area.

Another way of selectively altering the structural properties of a stent or stent-graft segment is shown in FIGS. 14A and 15. Extended struts (718) and (719) may be used to increase the axial stiffness of a stent-graft segment. Extended struts are formed by extending an apex on one turn of the undulating wire until it contacts an apex on an adjacent turn. This contact between an extended strut and the apex of an adjacent stent turn provides an added amount of axial stiffness. In a preferred embodiment, a layer of tape (not shown) is applied around the device in a helical pattern that covers each of the apexes of the extended struts. This additional layer of taping keeps the strut pairs together.

Referring to FIG. 14A, a first helical stent turn (720) and a second helical stent turn (721) have a generally undulating shape having apexes. An extended strut (718) of the stent turn (720) is formed having its apex near or in contact with the apex of the stent turn (721) directly below. The extended strut (719) is similarly formed by extending an apex of the stent turn (721) directly down to contact the apex in the turn below. This pattern in continued, each time spacing the extended strut over one undulation. This results in a helical pattern of extended struts down the length of the device. Of course, the extended struts may be arranged in patterns other than the helical configuration described.

A number of these patterns may be employed in any one segment or the extended strut pattern may be used in other segments to increase axial stiffness. Preferably the distally adjacent segment (746) on the main body component (700) and the axially stiff distal segment (750) on the contralateral leg component are constructed with extended struts as shown in FIG. 15.

Referring to FIG. 15, the distal end (702) may be sized to properly fit the inside diameter of the target artery, in this case the abdominal aortic artery. Typically the prosthesis is designed to have an unconstrained diameter slightly larger than the inside of the target vessel.

The ipsalateral and contralateral legs of the assembled bifurcated stent-graft (740) are typically the same size at their distal ends regardless of the size of the distal end (702) and undergo tapered sections (724) and (738) that taper to a diameter which corresponds approximately to the internal diameter of the iliac arteries. These tapered sections (724) and (738) are preferable to abrupt changes in diameter as they tend to produce superior flow dynamics.

After deployment, the assembled bifurcated stent-graft (740) must establish sufficient contact with the healthy vessel lumen on each side of the aneurysm (758) so that the device does not migrate or dislodge when subjected to the relatively high fluid pressures and flow rates encountered in such a major artery, especially when the body again becomes mobile after recovery. Further, sufficient contact must be made so that there is no leakage at the distal end (702), the ipsolateral leg hole (706) or the proximal end (736) of the contralateral leg.

Anchoring or staying features that allow the stent or stent-graft exterior to anchor itself to the vessel lumen wall may be provided to help the device seal to the vessel wall and maintain its deployed position. For example, anchors (716) as seen in FIGS. 14A and 15 are provided on the main body component (700) and could also be provided on the contralateral leg component (730). Preferably the top stent portion (717) is directed angularly outward. This flared stent portion works to force the anchors (716) into the vessel wall as the top stent portion (717) expands under force into radial interference with the vessel wall upon deployment.

Figure 17:
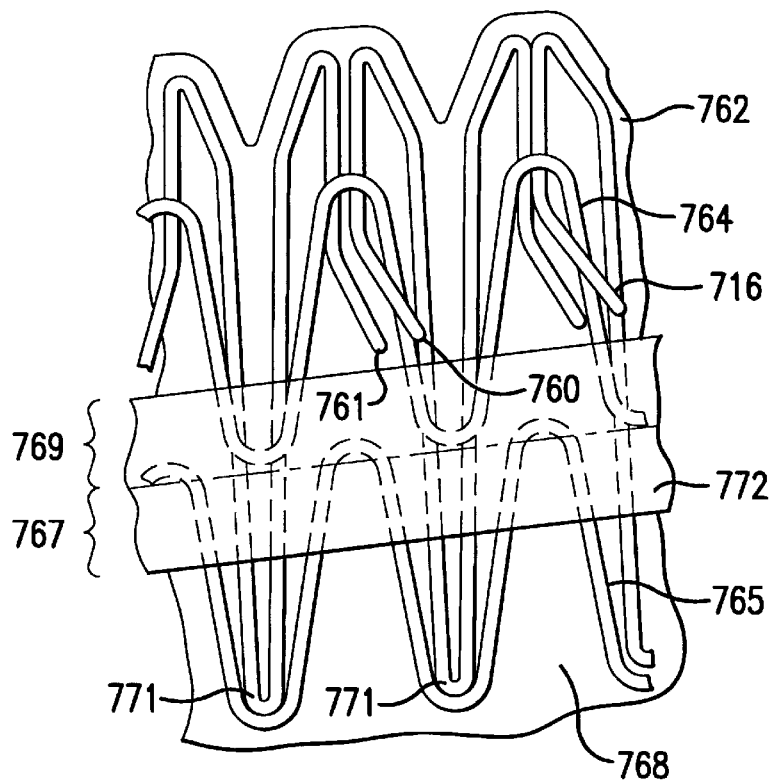
FIG. 17 is a perspective break-away view showing a close-up of a preferred construction of the stent anchoring apexes.

A preferred construction for an anchor (716) is shown in FIG. 17. This construction involves extending two wires from the upper stent turn (762) under an apex of an adjacent lower stent turn (764). The two ends of stent wires (760 and 761) are then bent out and away from the graft material (768). Extended struts (771) are formed adjacent to each anchor in the manner described above except the extended struts extend under the adjacent lower stent turn (764) down to a third stent turn (765). This extended strut arrangement provides support for the anchors (716) and provides for low stresses in the wires (760 and 761) under the application of bending forces encountered as the prosthesis expands into the vessel wall. The extended struts (771) minimize the localized deformation of the stent-graft structure in the area of the anchors by providing broader support.

Figure 16:
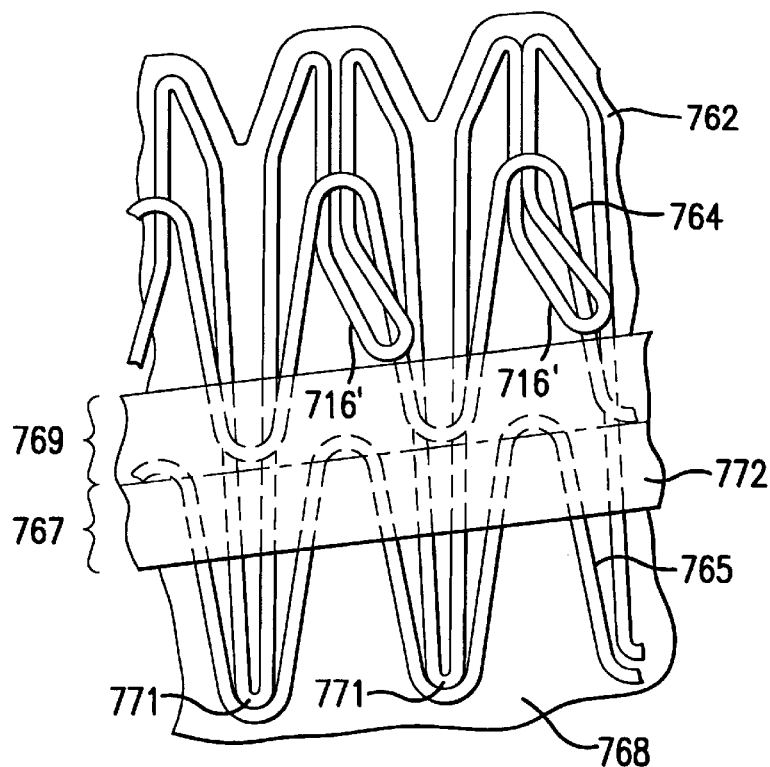
FIG. 16 is a perspective break-away view showing a close-up of one construction of stent anchoring apexes.

Another construction of the anchors (716') are shown in FIG. 16. An anchor (716') is formed in the same manner except the ends of the anchor remain connected in a 'U-shape' configuration as shown. An anchor (716') may be formed at any location on the stent-graft. Most preferably, the anchors are formed in an evenly spaced pattern around the top stent portion (717) (FIG. 14A).

It should be apparent that the anchors as described above are not limited in use to the stent-graft combination shown in the figures but indeed could be used in any non-bifurcated or stent only construction that require similar functionality.

Sealing at the vessel wall may also be enhanced by the alternate construction shown in FIG. 17 by way of a sealing mechanism. A sealing mechanism can be used with any type of implant, including any of the implants discussed above. For purposes of illustration, the sealing mechanism is shown with reference to the bifurcated implant of FIG. 14 and comprises seal member (772) as seen in detail in FIGS. 16 and 17. The sealing mechanism described below can be used with any of the implants discussed above.

One preferred construction for seal member (772) in the variations shown in FIGS. 16 and 17 may be similar to the preferred construction for the tape member used in constructing the stent-graft tubular member, as is provided in reference to FIG. 1 and FIG. 3 above.

In general, a thin walled ePTFE tape is used for seal member (772) similarly as that for tape member (128), shown variously in the previous figures. The tape used for seal member (772) is adhered to the outer surface of the stent-graft, including over tape member (128), described previously for bonding the stent and graft members. Seal member (772) has an inner surface constructed of a similar material for either the outer surface of the tape member (128) or the outer surface of the graft-member (124), depending upon which surface the seal member is desirably adhered.

First cuff end (767) is bonded to the stent-graft outer surface and second cuff end (769) is not, in order to form the unadhered flange to function as a oneway valve against peril-stent-graft flow. Seal member (772) may be selectively adhered along its length in this manner by providing a variable inner surface to the seal member such that, upon heating, only the surface in the region of first cuff end (767) bonds to the outer surface of the stent-graft. For example, the inner surface of seal member (772) may have an FEP liner in the region of first cuff end (767) but not in the region of second cuff end (769). In this case, upon contacting an outer surface of the stent-graft that has a uniform FEP outer surface, only first cuff end (767) may be heat secured thereon.

Alternatively, seal member (772) may have a uniform inner surface, such as constructed of FEP, and a variable outer surface, such as with a selective portion of FEP, may be provided either on the tape member (128) or on the graft member (124) in the region where the heat bonding of seal member (772) is desired. Still further, seal member (772) may have a uniform surface and may be positioned over tape member (128) and graft member (124) so that variability between the outer surfaces of tape member (128) and graft member (124) causes a selective bonding with the first cuff end (767) over one of those surfaces.

Further to the construction of seal member (772), the particular wall of thickness of the tape which may be used for this component should desirably be as thin as possible to functionally provide the flange-one-way-valve function for that member. This is because, since seal member (772) is over the outer surface of the other stent and graft components of the stent-graft, seal member (772) is believed to be the profile-limiting feature of the overall assembly. Therefore, in a particular design, seal member (772) may desirably be a thinner wall than for the tape member used to construct the stent-graft described in reference to FIGS. 1 and 3.

Further referring to the particular constructions and related methods just described for adhering seal member (772) to the outer surface of the underlying stent-graft, it should be apparent to one of ordinary skill in the art that the desired construction and heat securing technique for seal member (772) is premised upon the theory that, where one polymer meets a like polymer (such as FEP meeting FEP), heating under proper conditions will allow for a selected heat bond. Any suitable means may be used for securing a seal member to the outer surface of a given tublar member, as would be apparent to one of ordinary skill.

Further there is a plurality of circumferential strut spaces between the struts of the stent member. It is believed that these spaces may provide a path for leakage flow around the outer surface of the graft member and along the outside of the stent-graft. Second cuff end (769), however, captures such leakage flow beneath its flange, which can not propagate along the outer surface of the stent-graft because first cuff end (767) is secured to the outer surface of that stent-graft. In other words, flow over the stent-graft and into an aneurysm is occluded.

Furthermore, when anchor (716) is anchored into the wall of abdominal aortic artery as shown in FIG. 15, it has been observed that the portion of main body component (700) at and adjacent to the anchor (716) may be forced away from the artery wall. This action causes a separation between the outer surface of main body (700) and the artery wall, which separation is believed to create a leakage flow path. The flange of seal member (772) captures that flow and occludes it from propagating into the aneurysm (758).

In addition to maintaining a good contact with the vessel lumen walls, the components of the stent-graft must make sufficient contact with each other such that the separate modules stay attached and do not leak at their engagement interface. The stent-graft shown in FIG. 18 illustrates several important features designed to effectuate a leak-free and positionally stable seal at the interface between the receiving lumen (703) of the main body component (700) and contralateral leg component (730).

Figures 18, 19, 20:
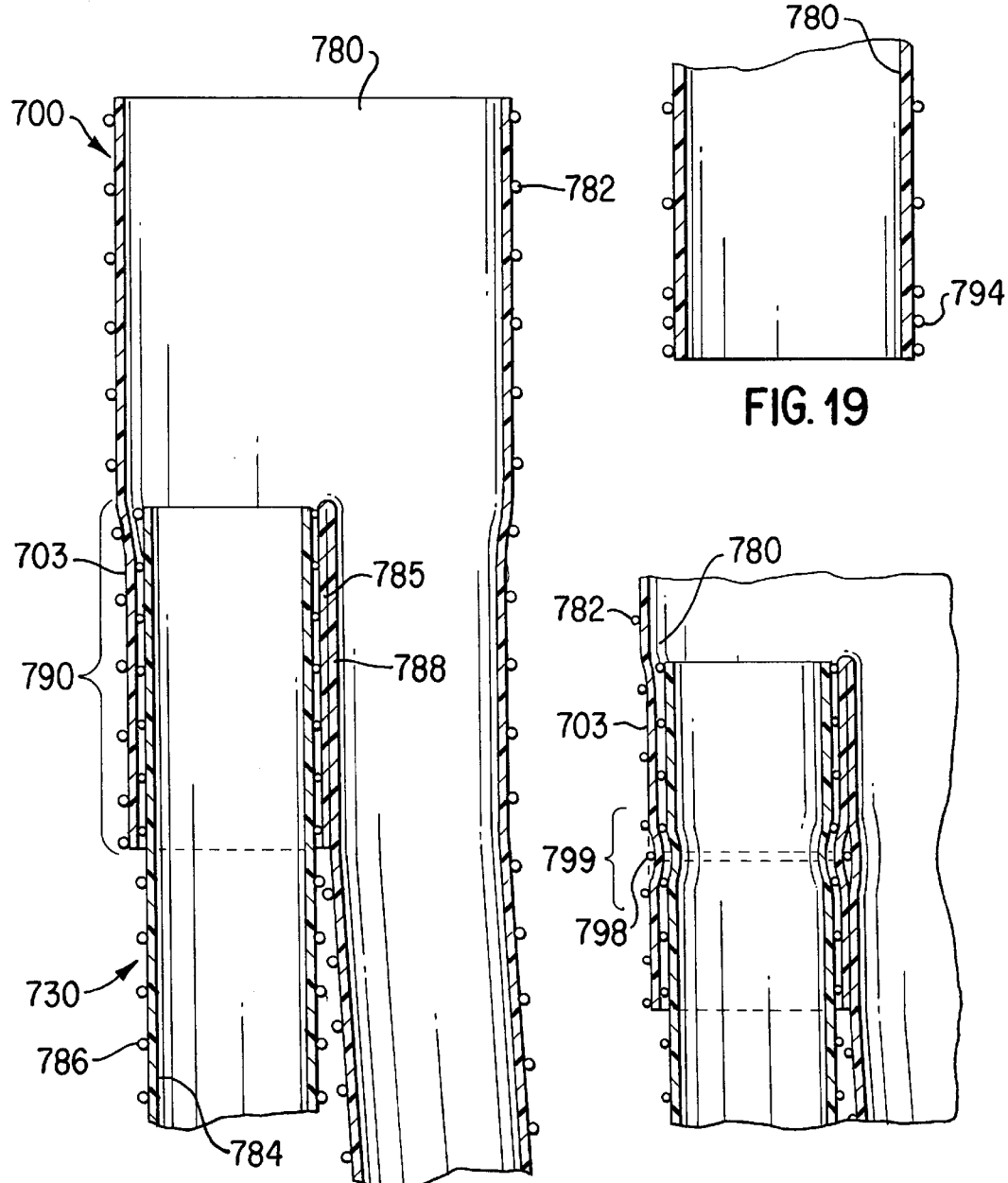
FIG. 18 is a cross-sectional view of the stent-graft of FIG. 14B taken along section line 18—18.
FIG. 19 is a cross-sectional view of the stent-graft of FIG. 14A taken along section line 19—19.
FIG. 20 is an enlarged partial cross-sectional view of the contralateral leg connection depicted in FIG. 18 having a localized zone of decreased diameter.

FIG. 18 shows a partial cross-section of the assembled stent-graft. The contralateral leg component (730) has been inserted into the receiving lumen (703) of the main body component (700). This cross-sectional view shows clearly that the main body component (700) includes a main body graft member (780) and a main body stent member (782). The contralateral leg component (730) includes a contralateral graft member (784) and a contralateral stent member (786).

At the interface between the contralateral leg component (730) and the receiving lumen (703), the assembly provides for an extending sealing region (790). Preferably the extended sealing region (790) consists of a generally cylindrical interfering friction fit between the outside diameter of the contralateral leg component (730) and the inside diameter of the receiving lumen (703). That is, the natural or resting outside diameter of the self expanding contralateral leg component (730) would be larger than the natural inside diameter of the receiving lumen (703). Thus the forces created by the interference act to seal the two components and also serve to resist movement of the two components.

The type of generally cylindrical extended sealing region just described has many advantages. First, it allows for the stent and graft structures in the extended sealing region (790) to be constructed of relatively simple generally cylindrical elements that are easily manufactured. Because the extended sealing region (790) extends over a large length it necessarily has a large surface area to effectuate sealing between the components. This larger sealing area typically provides that multiple turns of the stent structures will be engaged in an interfering and thus sealing relationship.

In one preferred embodiment, the extended sealing region has a length in excess of one-half of the diameter of the receiving lumen (703), more preferably the length is greater than the diameter of the receiving lumen (703), and most preferably the length is more than 2 times the diameter of the receiving lumen (703).

Because the manufacturing tolerances of the simplified shapes are easily controlled and because the engagement of the extended sealing region (790) is quite large, a highly reliable joint is formed between the modular components. Even so it may be desirable to create one or more localized zones of increased interference to increase the sealing capability and positional stability.

Localized zones of interference may be created in a number of ways. In a preferred embodiment, an annular ring of decreased diameter is formed within the receiving lumen. Such a localized decreased diameter causes a greater interference with the outside diameter of the contralateral leg component in a localized area while the remainder of the engagement with the receiving lumen is subject to the general interference friction fit described above.

One way of creating a localized decreased diameter is illustrated in FIG. 20 which shows a partial cross-section of the extended sealing region (790). A zone of reduced diameter (799) is created by placing an anchoring ring (798) between the graft member (780) and the stent member (782) of the receiving lumen (703). The anchoring ring may be made from any polymeric or wire material, preferably a material that will not inhibit the receiving lumen from self-expanding to an open position. Most preferably the material is a suture material, typically ePTFE.

Figure 21:
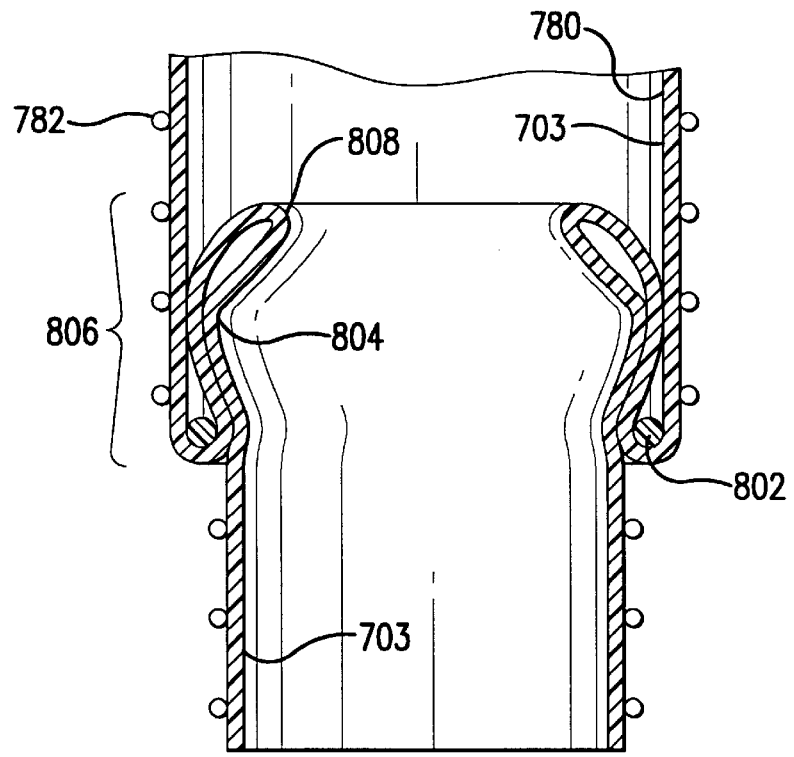
FIG. 21 and FIG. 22 are enlarged partial cross-sectional views of alternative constructions of the receiving lumen.
Figure 22:
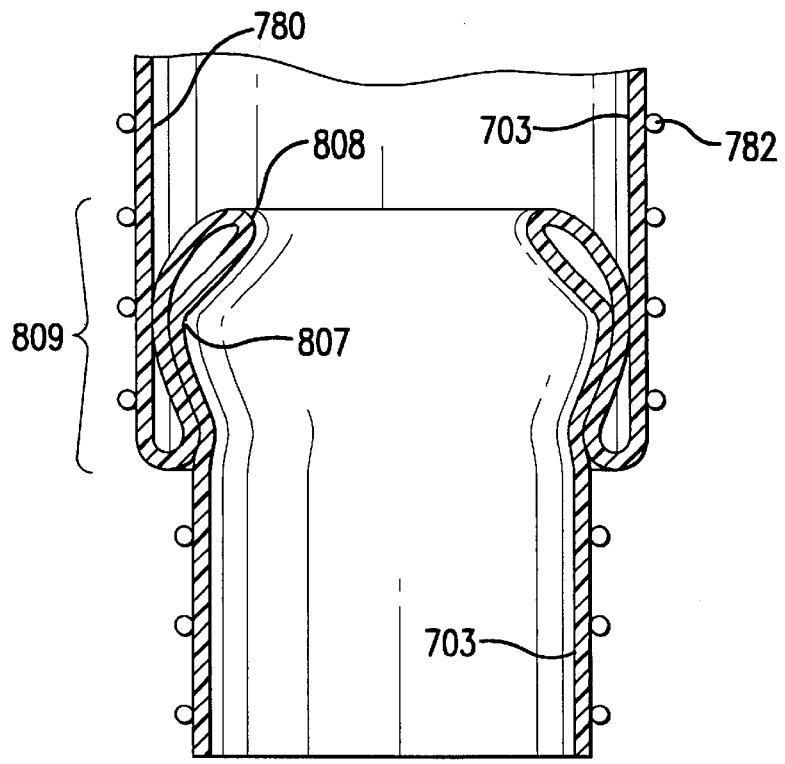

Alternately, localized zones of decreased diameter may be created as shown in FIGS. 21 and 22 by folding a portion of the graft member (780) back up into the receiving lumen (703). In FIG. 21, the zone of reduced diameter (806) is formed by creating a folded flap (808) of the graft member (780) around an anchoring ring (802). The flap is heat bonded in place roughly at a location (804) as shown. In FIG. 22, the zone of reduced diameter (809) is formed of flap (808) and heat bonded roughly at a location (807) in a similar manner but without any anchoring ring. The localized interference using these methods tends to cover a larger area and the flap (808) provides a more flexible member to seal against the outside diameter of the contralateral leg component (730).

Figure 23:
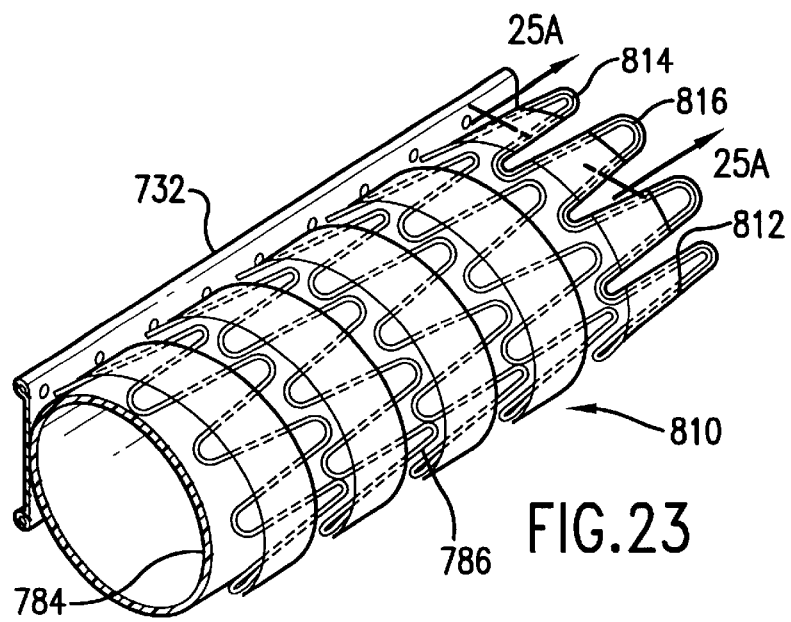
FIG. 23 is a partial perspective view of an alternate scalloped construction of the distal region of the contralateral leg component.

One further aspect of ensuring a good seal between the stent-graft components involves the use of a scalloped stent-graft construction at the distal end of the contralateral leg component (810). To create this scalloped construction, the graft material between the apexes of the stent member is removed on the last turn of the stent. For example scallop (812) may be formed by removing (or cutting and folding under) the graft material from between a first apex (814) and an adjacent apex (816) as shown in FIG. 23.

Figure 24A:
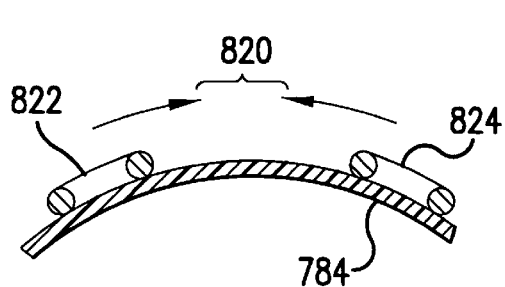
FIGS. 24A and 24B are cross-sectional views taken along section line 24A—24A as shown in FIG. 14A depicting a free state and a forced state respectively.
Figure 25A:
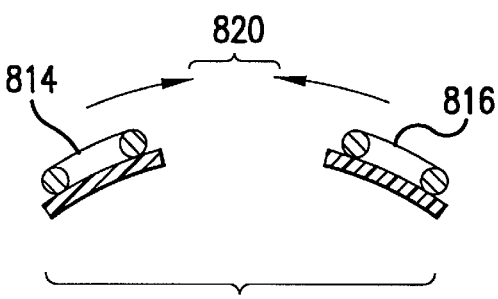
FIGS. 25A and 25B are cross-sectional views taken along section line 25A—25A as shown in FIG. 23 depicting a free state and a forced state respectively.
Figure 24B:
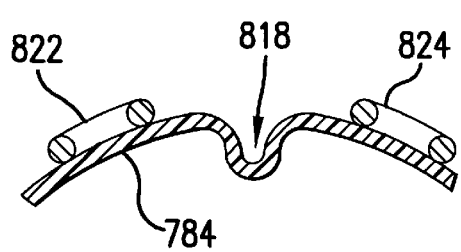
Figure 25B:
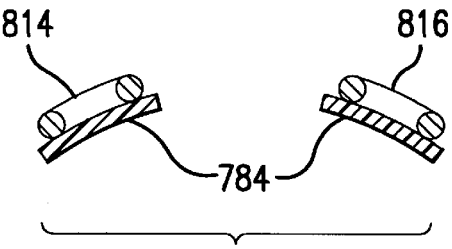

The advantages of using a scalloped arrangement are illustrated in FIGS. 24A through 25B. FIG. 24A shows a cross-section of the fully expanded contralateral leg component (730) having an unscalloped construction. A first apex (822) and an adjacent apex (824) have continuous graft material (784) in the area between them. When the apex (822) and the adjacent apex (824) are forced together in the directions of the arrows (820), the graft material (784) forms a buckle or wrinkle (818) which is a potential leak path or is a potential site for thrombogenic material to build up as seen in FIG. 24B. The scalloped construction shown in FIGS. 25A and 25B, on the other hand, have no graft material between the first apex (814) and the adjacent apex (816) and therefore when forced together do not form a graft material wrinkle.

The wrinkle (818), mentioned above may also be formed when the stent-graft is not allowed to expand to its complete diameter. For instance it is quite common that the receiving lumen or vessel wall internal diameter is smaller than the fully expanded stent-graft outer diameter. This being the case, it should be clear that the scalloped construction may alternately be used at any of the terminal openings of the main body component or the contralateral leg component. Preferably, the distal end (702) of the main body component (700) also has this scalloped construction as shown in FIGS. 14A and 14B.

Figure 27A:
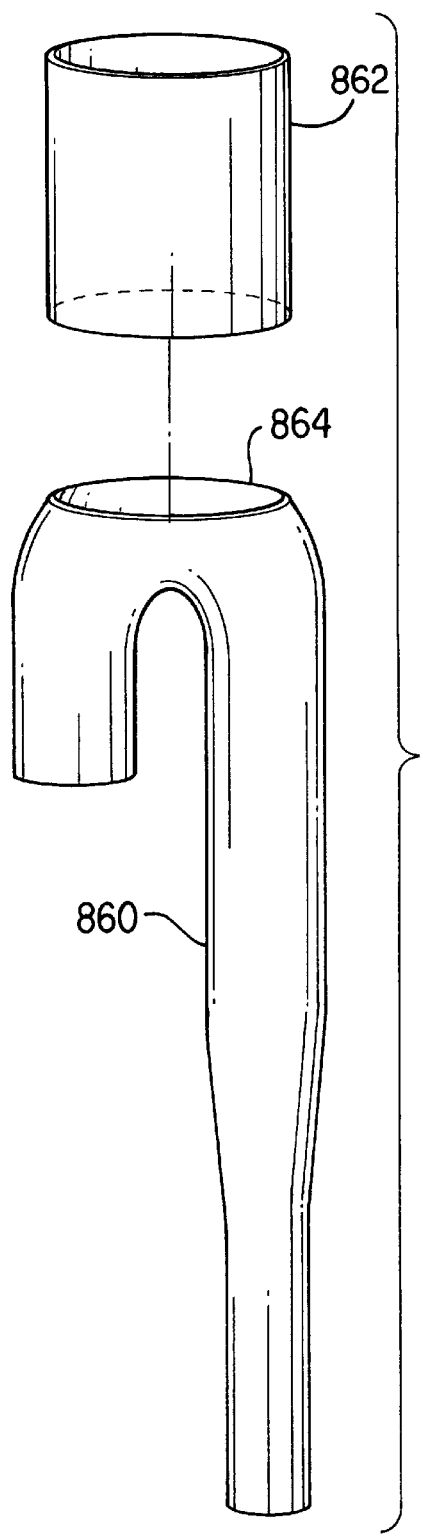
FIG. 27A is a front view of the unassembled components of an alternate construction of the graft element.
Figure 27B:
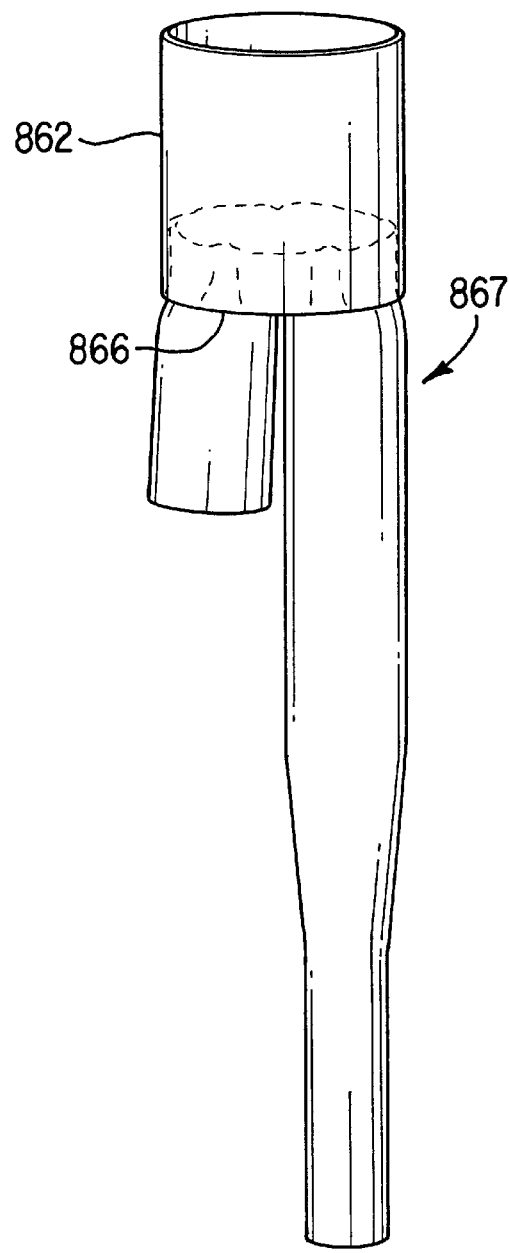
FIG. 27B is a front view of the assembled graft element according to the alternative construction of FIG. 27A.

In the previous discussion we have referred generally to a stent-graft that includes a graft member. While the construction of such straight stent grafts are discussed at length above, the construction of a bifurcated graft member is illustrated in FIGS. 26, 27A and 27B. A bifurcated graft member suitable for construction of the main body component (700) discussed above is generally formed of two graft members: the ipsalateral tapered graft (840) and the contralateral tapered graft (842). The separate contralateral leg graft component (844) is a straight or tapered section and may be formed according to the principles discussed in the first section above.

The ipsalateral tapered graft (840) has three sections which are separated by tapers. A top section (846), a middle section (848), and a bottom section (850). The body component graft (854) is formed by heat bonding the top section (846) of ipsalateral tapered graft (840) to the top section (847) of contralateral tapered graft (842). This heat bonding forms a common septum (856) which in a preferred embodiment is subsequently cut away to produce a smooth bifurcation. Cutting away the septum material prevents fluid flow disturbance or blockage that could result from deviation of the septum. Such deviation is caused by the fluid pressure and is aggravated if the stent-graft is radially compressed in a manner which causes the septum to become loose or no longer taut.

In another embodiment, a graft section may be constructed in the manner illustrated in FIGS. 27A and 27B. According to this embodiment, the body component graft (867) is constructed from two pieces. A tubular graft section (860) is bent into a 'U-shape'. A top hole (864) is formed by notching the top of the 'U-shape'. Upper graft section (862) is placed over the top hole (864) of tubular graft section (860). The two pieces are bonded together at the bonding interface (866). Preferably, the two graft pieces are heat bonded while supported by interior mandrels (not shown) to obtain the desired shape and smooth interior. However, upper graft section (862) may be attached to the tubular graft section (860) at the bond interface (866) in any manner that provides a sufficiently leak free seal. For example the components may be sutured together or adhesive bonded.

Figure 28C:
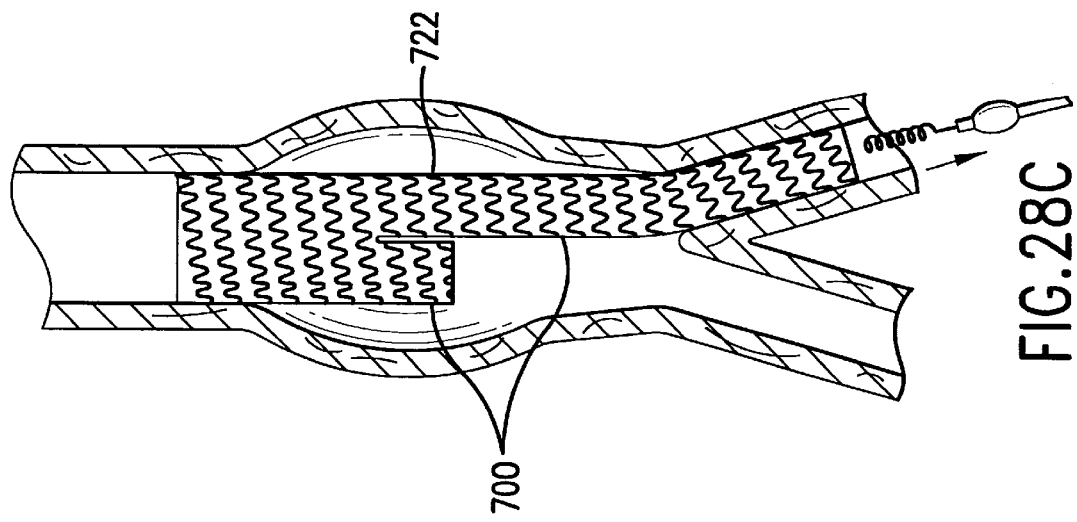
FIGS. 28A through 28E diagrammatically show deployment of a bifurcated stent-graft.

In use, the modular bifurcated stent-graft is typically delivered percutaneously through the vasculature of the body. Preferably the prosthesis is delivered by way of a restraining member as described in detail above. FIGS. 28A though 28E diagrammatically illustrate deployment of a bifurcated stent-graft with a restraining member (902) using a percutaneous catheter assembly. Referring to FIG. 28A, a multilumen catheter assembly (928) has been inserted to a selected site within a body lumen. The main body component (700) of a bifurcated stent-graft is held in a compressed state about a guidewire (926) and a guidewire lumen (929) by a restraining member (902) and a coupling member (906). The collapsed main body component (700) is held axially in place prior to deployment by a distal barrier (930) and a proximal barrier (932). The distal (930) and proximal (932) barriers are typically affixed to the guidewire lumen (929). The coupling member (906) extends through the eyelets (920) of the restraining member (902) forming chain knots and into the multilumen catheter (928).

FIG. 28A shows advancement of the multilumen catheter (928) with the distally located main body component (700) and the restraining member (902) into implantation position, typically at the bifurcation of a major vessel. During deployment it is critical that the surgeon align the main body component (700) so that the ipsalateral leg (726) will extend down one branch of the bifurcated vessel, and so the receiving hole (704) and the receiving lumen (703) will be lined up with the other branch of the bifurcated vessel so as to receive the contralateral leg component (730).

One way of facilitating this alignment is to provide radiopaque markers so that the surgeon may readily determine the rotational position of the main body component (700) prior to deployment or release from the restraining member (902). In a preferred embodiment, a long marker (934) is located on the contralateral side of the compressed assembly and a shorter marker (936) is placed on the ipsalateral side. Preferably these markers are placed on the stent prior to compression but may alternatively be part of the restraining member. Having one marker of a different length allows the surgeon to identify the orientation of both the ipsalateral leg and the receiving lumen relative to the bifurcated vessel.

Once the assembly is properly aligned and positioned for implantation, the coupling member (906) is pulled and the restraining member (902) begins to release the implant, typically at the distal end first. In the preferred embodiment, the restraining member (902) is located down the side as shown because it is less likely to interfere with deployment of the receiving lumen (703).

Figure 28B:
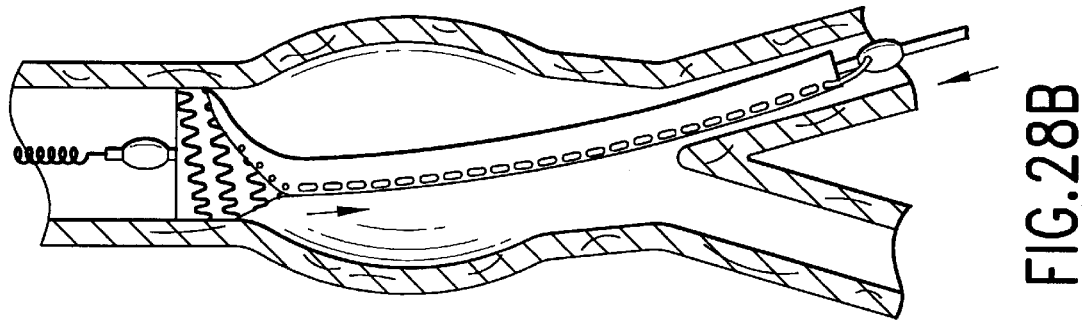
Figure 28A:
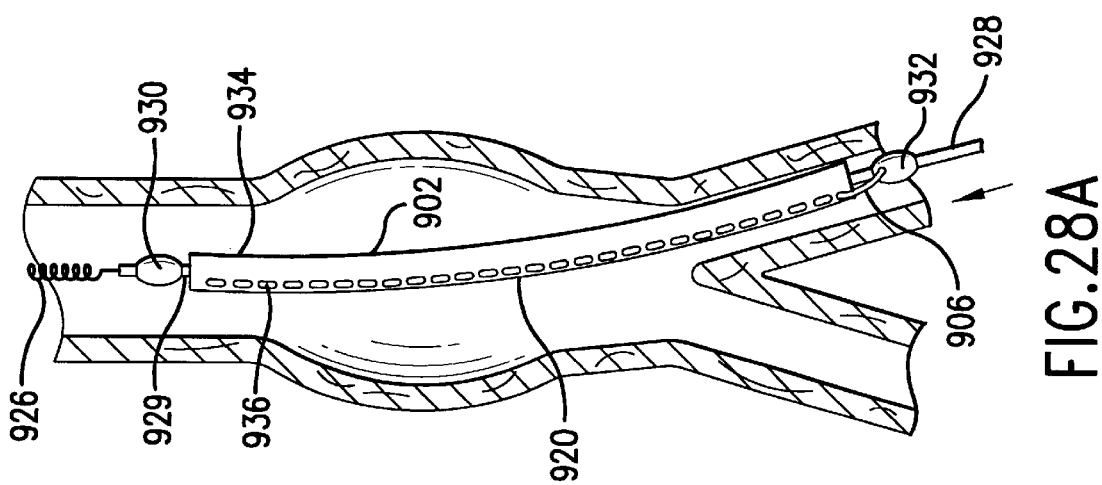

FIG. 28B shows the main body component (700) radially expanding as the coupling member (906) is retracted through the eyelets (920) of the restraining member (902) and into the catheter assembly (928). In the preferred embodiment, the restraining member (902) has been fixedly attached to the main body component (700) with a number of sutures along the length of the main body component to prevent any relative longitudinal movement between the implanted prosthesis and the restraining member (902). The restraining member may optionally employ a retracting or pull-down mechanism as described at length above.

FIG. 28C shows the main body component (700) and the restraining member (902) in final implantation position at the vessel bifurcation after the guidewire (926) and the catheter assembly (928) have been retracted.

Figure 28E:
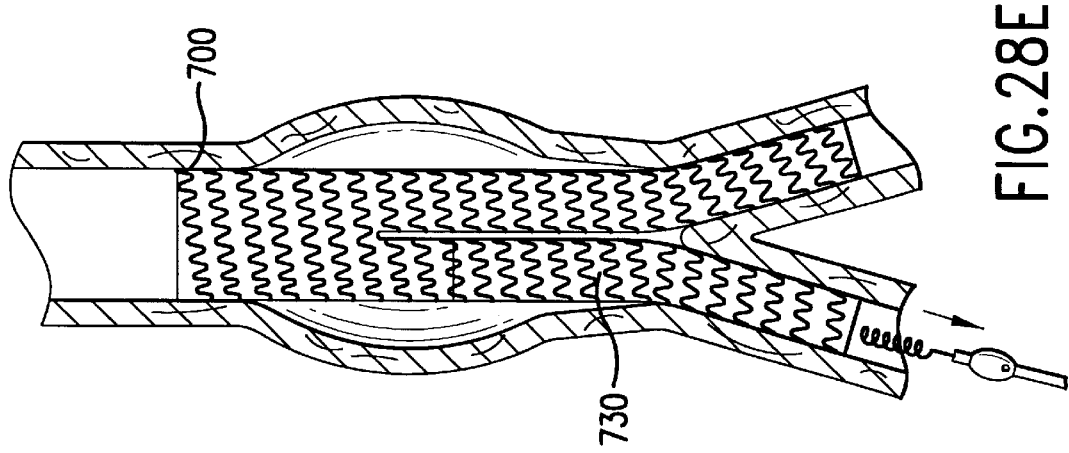
Figure 28D:
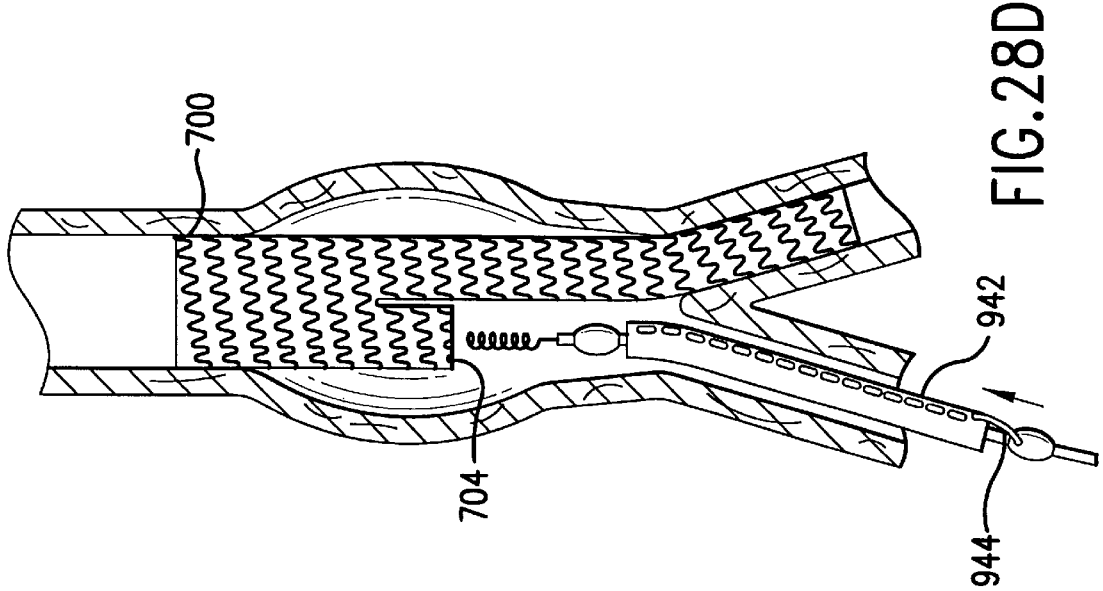
Figure 29A:
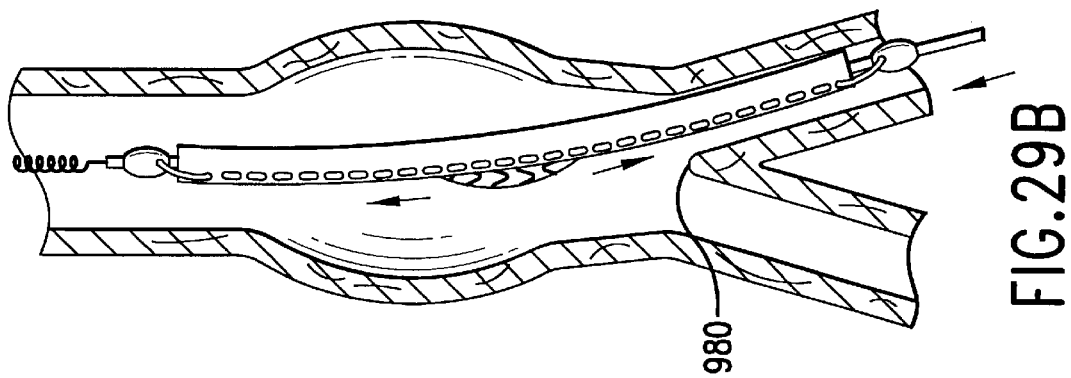
FIGS. 29A, 29B, 29C, and 29D diagrammatically show deployment of a bifurcated stent-graft using an alternate delivery system.
Figure 29B:
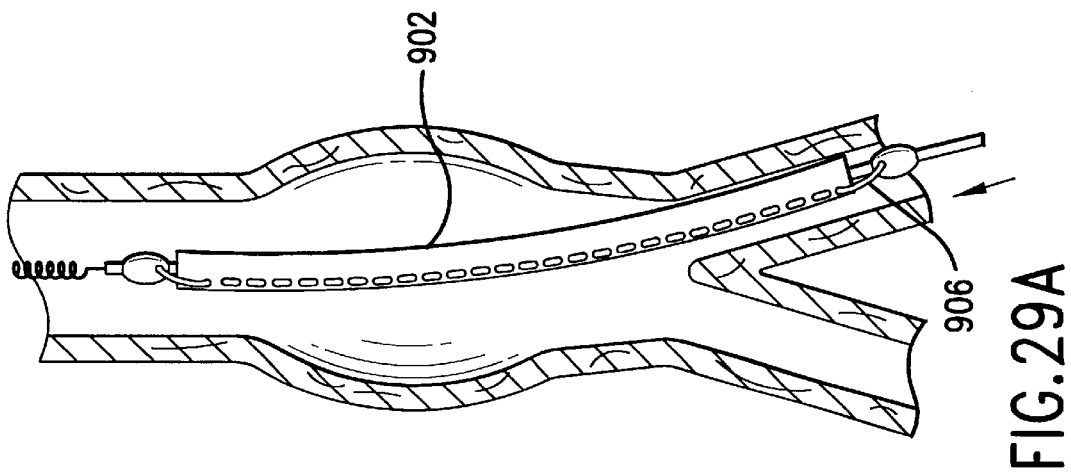
Figure 29D:
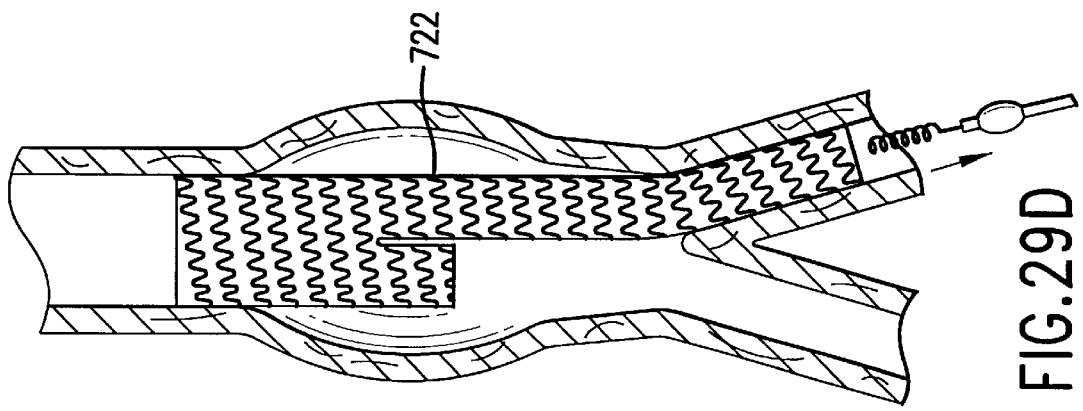
Figure 29C:
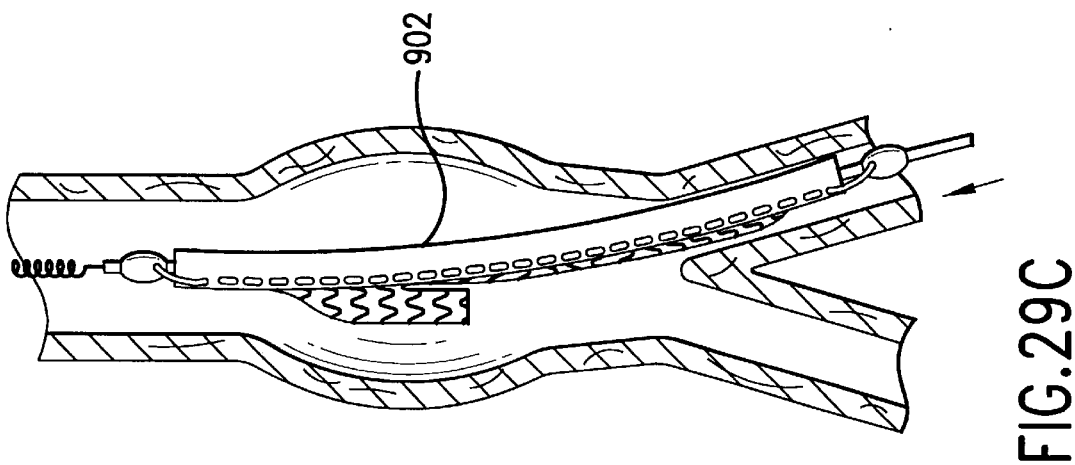

FIG. 28D shows the contralateral leg component (730) being delivered to the contralateral receiving hole using a restraining member (942). The procedure for positioning and releasing the contralateral leg component (730) is the same as that described above for implantation of a generally cylindrical stent-graft except that certain radiopaque markers may be employed to ensure its proper position relative to the bifurcation point (728) of main body component (700).

Radiopaque markers may be located, for example, to indicate the position of the receiving hole (704), the distal end (734) of the contralateral leg component (730), and the bifurcation point (728) of the main body component (700). These markers serve to indicate the position of the contralateral leg component as it enters the receiving hole (704) and its ultimate position relative to the receiving lumen (703) which begins at bifurcation point (728). In a preferred embodiment illustrated in FIG. 19, the radiopaque wires (794) may be heat bonded or imbedded into the graft material (780) around the periphery of the receiving lumen. Such radioopaque wires could be used in other places such as the contralateral leg component lumen, the ipsalateral leg lumen or the lumen at the distal end of the main body component (700).

FIG. 28E shows the assembled bifurcated stent-graft in its final implantation state with the contralateral leg component expanded into and engaged with the receiving lumen of the main body component (700).

FIGS. 29A through 29D diagrammatically show the same stent or stent-graft components being deployed except that the restraining member (902) is released from the center out towards as the coupling member (906) is retracted. This may provide more accurate placement relative to the bifurcation point of the vessel instead of relative to the distal end as with end release.

While this invention has been described with reference to illustrative embodiments, this description is not intended to be construed in a limiting sense. Various modifications and combinations of the illustrative embodiments, as well as other embodiments of the invention will be apparent to persons skilled in the art upon reference to the description. It is therefore intended that the appended claims encompass any such modifications or embodiments.

The disclosures of the publications and patents that are cited in this application are hereby incorporated by reference.

What is claimed is:

1. A device, comprising:
    an expandable implant;
    a sheet of material wrapped around said expandable implant, said sheet having first and second major surfaces and a plurality of openings extending from said first major surface to said second major surface; and
    a coupling member cooperating with said openings for releasably coupling portions of the sheet to one another to maintain said expandable implant in a collapsed state.

2. The device of claim 1 wherein said sheet of material has a length and a width, said width being less than about 40 mm.

3. The device of claim 1, wherein said portions include side margins extending between longitudinal ends of said sheet of material, and at least two of said plurality of openings comprise eyelets disposed along at least one of said side margins.

4. The device of claim 3, wherein said eyelets are holes formed in said side margin.

5. The device of claim 3, including a loop coupled to said sheet, said loop forming said at least one of said eyelets.

6. The device of claim 3 wherein said coupling member comprises a thread adapted for threading through said eyelets.

7. The device of claim 1 wherein said implant comprises a stunt.

8. The device of claim 3, further including a reinforcing member, said reinforcing member being disposed between at least one of said eyelets and an outer perimeter of the side margin in which said at least one of said eyelets is disposed.

9. The device of claim 6, wherein at least one of said side margins comprises overlapping portions of said sheet, wherein a reinforcing member is positioned between said overlapping portions.

10. A device, comprising:
    an expandable implant;
    a sheet of material wrapped around said expandable implant;
    a coupling member for releasably coupling portions of the sheet to one another to maintain said expandable implant in a collapsed state, wherein said portions include side margins extending between longitudinal ends of said sheet, and at least one opening is disposed along each of said side margins; and
    a reinforcing member disposed between said at least one opening and an outer perimeter of the side margin.

11. A device, comprising:
    an expandable implant;
    a sheet of material wrapped around said expandable implant;
    a reinforcing member; and
    a coupling member for releasably coupling portions of the sheet to one another to maintain said expandable implant in a collapsed state, wherein said portions include side margins extending between longitudinal ends of said sheet of material, and at least one opening is disposed along each of said side margins, wherein at least one of said side margins comprises overlapping portions of said sheet, said reinforcing member being positioned between said overlapping portions.

12. The device of claim 11, wherein said coupling member comprises a thread adapted for threading through said at least one opening.

13. An assembly, comprising:
    an implant having a collapsed state and an expanded state and including a stent; and
    a sheet of material attached to said implant, said implant being in said collapsed state and having said sheet of material wrapped around at least a portion thereof, said sheet having ends and margin portions extending between said ends, said margin portions being releasably coupled to one another.

14. The assembly of claim 13 further including a discrete coupling member, said coupling member coupling said margin portions to one another.

15. The assembly of claim 13 wherein said sheet is arranged in generally tubular form to maintain said stent in said collapsed state.

16. The assembly of claim 13, wherein said sheet of material includes first and second major surfaces and a plurality of openings extending from said first major surface to said second major surface.

17. The assembly of claim 14, wherein the coupling member comprises a filament or thread-like element that forms at least one releasable knot.

18. A method for deploying a prosthesis in a lumen comprising the steps of:
    (a) providing an expandable stent which is coupled to and restrained in a collapsed state by a restraining member, (b) positioning said collapsed and restrained stent in a lumen having a wall, (c) releasing said restraining member, and (d) expanding said stent into a deployed configuration and urging said restraining member into a position against said wall.

19. The method of claim 18 wherein the stent is a self-expanding stent that is allowed to self-expand to urge the restraining member into a position against said wall.

20. The method of claim 18, wherein said restraining member includes first and second major surfaces and a plurality of openings extending from said first major surface to said second major surface.

21. The method of claim 18, wherein said restraining member includes side margins coupled together by a filament or thread-like element, which forms at least one releasable knot.

22. A method of assembling an implant, comprising the steps of:

placing a collapsed implant in a sheet of material having longitudinally extending side margins, said sheet having first and second major surfaces and a plurality of openings extending from said first major surface to said second major surface; and coupling said side margins to each other to maintain said implant in a collapsed configuration.

23. The method of claim 22, wherein said coupling step comprises coupling said side margins with multiple elements such that multiple portions of the side margins may be released simultaneously.

24. A method of assembling an implant, comprising the steps of:

placing a collapsed implant in a sheet of material having longitudinally extending side margins; and coupling said side margins to each other to maintain said implant in a collapsed configuration, wherein said coupling step comprises coupling said side margins with multiple elements such that multiple portions of the side margins may be released simultaneously.

25. A method for collapsing an expandable stent into a generally tubular restraining member comprising the steps of:

(a) pulling the stent through a tapered construct which radially collapses the stent, and (b) positioning the stent into a restraining member, said restraining member having first and second major surfaces and a plurality of openings extending from said first major surface to said second major surface.

26. The method of claim 25 wherein a portion of said stent is folded before step (a).

27. A device, comprising:

a tubular support;

a sheet member attached to said tubular support and having at least one connectable free end; and a coupling member for releasably connecting said at least one free end to said sheet member to maintain said support in a collapsed state.

28. The device of claim 27, wherein said sheet member has one free end.

29. The device of claim 27, wherein said sheet member has two free ends.

30. The device of claim 27, wherein said support includes a stent member.

31. The device of claim 28, wherein said support includes a graft member.

32. The device of claim 29, wherein sheet member is dimensioned to maintain said tubular support in a collapsed configuration when said free ends are connected to one another.

33. The device of claim 29, wherein said free ends include side margins extending between longitudinal ends, and at least one eyelet is disposed along each of said side margins.

34. The device of claim 33 wherein said coupling member extends through said eyelets to maintain said support in a collapsed configuration.

35. The device of claim 27 wherein the support comprises a stent-graft.

36. The device of claim 27, wherein said sheet member includes first and second major surfaces and a plurality of openings extending from said first major surface to said second major surface.

37. The device of claim 27, wherein said coupling member comprises a filament or thread-like element, which forms at least one releasable knot.

38. An assembly comprising:

a stent-graft having a collapsed and an expanded state; and an attached restraining member, said restraining member adapted to be wrapped around at least a portion of said stent-graft and having longitudinally extending side portions adapted to be releasibly coupled to each other to maintain said stent-graft in its collapsed state.

39. The assembly of claim 38 wherein said restraining member is a sheet of a polymeric material and has a length, width and thickness, said width being less than an expanded diameter of said stent-graft.

40. The assembly of claim 39 wherein said sheet has a width that is less than about 40 mm.

41. The assembly of claim 39 wherein the length of said restraining member, measured along a longitudinal axis thereof, is less than or equal to a length of said stent-graft.

42. The assembly of claim 38 further including a discrete member for releasably coupling said portions to one another.

43. The assembly of claim 42, further including:

means for multidirectionally releasing the discrete member between said side portions.

44. The assembly of claim 38, wherein said side portions include side margins extending between respective ends of said stent-graft and contain at least one eyelet.

45. The assembly of claim 44 wherein said eyelet is formed by a hole formed in said margin.

46. The assembly of claim 44 wherein said eyelet comprises a loop coupled to said restraining member.

47. The assembly of claim 38, wherein said restraining member includes first and second major surfaces and a plurality of openings extending from said first major surface to said second major surface.

48. The assembly of claim 38, wherein said side portions are adapted to be releasably coupled by a coupling member comprising a filament or thread-like element, which forms at least one releasable knot.

49. A device, comprising:

an expandable implant;

a sheet of material wrapped around said expandable implant; and a coupling member for releasably coupling portions of the sheet to one another to maintain said expandable implant in a collapsed state, wherein the coupling member comprises a filament or thread-like element that forms at least one releasable knot.

50. A device, comprising:

an expandable implant;

a sheet of material wrapped around and attached to said expandable implant; and a coupling member for releasably coupling portions of the sheet to one another to maintain said expandable implant in a collapsed state.

51. A method of assembling an implant, comprising the steps of:

placing a collapsed implant in a sheet of material having longitudinally extending side margins; and coupling said side margins to each other with a filament or thread-like element that forms at least one releasable knot to maintain said implant in a collapsed configuration.

52. A method of assembling an implant, comprising the steps of:

placing a collapsed implant in a sheet of material having longitudinally extending side margins;

coupling said side margins to each other to maintain said implant in a collapsed configuration; and attaching said implant to said sheet of material.

53. A method for collapsing an expandable stent into a generally tubular restraining member comprising the steps of:

(a) pulling an expandable stent through a tapered construct which radially collapses the stent;

(b) positioning the stent into a restraining member having side margins; and (c) coupling said side margins together with a filament or thread-like element and forming at least one releasable knot to maintain said stent in a collapsed configuration.

54. A method for collapsing an expandable implant into a generally tubular restraining member comprising the steps of:

(a) pulling an expandable implant through a tapered construct which radially collapses the implant;

(b) positioning the implant into a restraining member having side margins; and (c) attaching the implant to said restraining member.

* * * * *